United States Patent
Saffie et al.

(10) Patent No.: US 8,088,401 B2
(45) Date of Patent: Jan. 3, 2012

(54) COMPOSITE MATERIAL COMPRISING A POROUS SEMICONDUCTOR IMPREGNATED WITH AN ORGANIC SUBSTANCE

(75) Inventors: Roghieh Saffie, Malvern (GB); Leigh Canham, Malvern (GB)

(73) Assignee: Psimedica Limited, Malvern, Worcestershire (GB)

(*) Notice: Subject to any disclaimer, the term of this patent is extended or adjusted under 35 U.S.C. 154(b) by 1490 days.

(21) Appl. No.: 10/576,448

(22) PCT Filed: Oct. 21, 2004

(86) PCT No.: PCT/GB2004/004460
§ 371 (c)(1),
(2), (4) Date: Aug. 11, 2006

(87) PCT Pub. No.: WO2005/042023
PCT Pub. Date: May 12, 2005

(65) Prior Publication Data
US 2007/0071787 A1 Mar. 29, 2007

(30) Foreign Application Priority Data
Oct. 21, 2003 (GB) .................................. 0324482.9
Oct. 21, 2003 (GB) .................................. 0324483.7

(51) Int. Cl.
*A61F 2/02* (2006.01)
(52) U.S. Cl. .................................................... 424/423
(58) Field of Classification Search .................. None
See application file for complete search history.

(56) References Cited

U.S. PATENT DOCUMENTS

| 6,666,214 B2 * | 12/2003 | Canham ........................ 128/899 |
| 7,763,277 B1 * | 7/2010 | Canham et al. ............... 424/489 |
| 2003/0134424 A1 | 7/2003 | Canham et al. |
| 2003/0170280 A1 | 9/2003 | Canham et al. |

FOREIGN PATENT DOCUMENTS

| WO | WO 97/06101 | * 2/1997 |
| WO | 02/067998 | 9/2002 |
| WO | 03/011251 | 2/2003 |

OTHER PUBLICATIONS

Karlsson et al, *Penetration and loading of human serum albumin in porous silicon layers with different pore sizes and thicknesses*, Journal of Colloid and Interface Science, Oct. 1, 2003, vol. 266, No. 1, pp. 40-47, XP002318975.

Foraker et al., *Microfabricated porous silicon particles enhance paracellular delivery of insulin across intestinal Caco-2 cell monolayers*, Pharmaceutical Research, Jan. 2003, vol. 20, No. 1, pp. 110-116, XP002318976.

* cited by examiner

*Primary Examiner* — Carlos Azpuru
(74) *Attorney, Agent, or Firm* — Nixon & Vanderhye P.C.

(57) ABSTRACT

The invention provides a composite material comprising a porous semiconductor impregnated with at least one beneficial organic substance, wherein the beneficial organic substance is present in an amount of at least 15% by weight, based on the weight of the material. Also provided are methods for the preparation of such materials, pharmaceutical compositions comprising them and their use in methods of treatment.

14 Claims, 18 Drawing Sheets

COMPOSITE MATERIAL COMPRISING A POROUS SEMICONDUCTOR IMPREGNATED WITH AN ORGANIC SUBSTANCE

This application is the US national phase of international application PCT/GB2004/004460 filed 21 Oct. 2004, which designated the U.S. and claims benefit of GB 0324483.7 filed 21 Oct. 2003, and GB 0324482.9 filed 21 Oct. 2003, the entire contents of each of which are hereby incorporated by reference.

FIELD OF THE INVENTION

The present invention relates to a composite material comprising a porous semiconductor. More particularly, the present invention relates to a composite material comprising porous semiconductor impregnated with high levels of a beneficial organic substance. It also relates to methods for the preparation of such materials, pharmaceutical compositions comprising them and their use in methods of treatment.

BACKGROUND TO THE INVENTION

There has been considerable interest within the pharmaceutical industry in the development of dosage forms which provide for the controlled release of beneficial substances over a period of time. Releasing an active substance in this way can help to improve bioavailability and ensure that appropriate concentrations of the substance are provided for a sustained period without the need for repeated dosing. In turn, this also helps to minimise the effects of patient non-compliance which is frequently an issue with other forms of administration.

Generally speaking, controlled release formulations are based on polymer material systems. Commonly, the active ingredients are incorporated into polymer and sol-gel systems by entrapment during synthesis of the matrix phase. Microencapsulation techniques for biodegradable polymers include such methods as film casting, moulding, spray drying and extrusion, melt dispersion, interfacial deposition, phase separation by emulsification and solvent evaporation, air suspension coating, pan coating and in-situ polymerization. Melt dispersion techniques are described, for example, in U.S. Pat. No. 5,807,574 and U.S. Pat. No. 5,665,428.

Less commonly, the active ingredient is loaded after formation of the porous matrix is complete. Such carrier systems generally have micron-sized rather than nanometer-sized pores. U.S. Pat. No. 6,238,705, for example, describes the loading of macroporous polymer compositions by simple soaking in a solution of the active ingredient and U.S. Pat. Nos. 5,665,114 and 6,521,284 disclose the use of pressure to load the pores of implantable prostheses made of polytetrafluoroethene (PTFE).

The problem of achieving high loading of the active ingredient limits the effectiveness of many currently known polymer based delivery systems. Various approaches to overcoming this issue have been described. U.S. Pat. No. 5,718,922, for example, discloses forming drug microspheres in a polymer/oil dispersion with a hydrophilic drug suspended in the oil phase, the oil preventing partition during microsphere formation such that a high drug loading can be achieved. In U.S. Pat. No. 6,319,381 there is described a technique for loading drugs into a porous metal prosthesis such as a stent. Here, the drug is first added to a first fluid that is a solvent of high capillary permeation, gross surface deposits are then removed by mechanical agitation in a second fluid that is a non-solvent of low capillary permeation and finally the prosthesis is rinsed in a third fluid that is a solvent for the drug but which once again has a low capillary permeability.

The use of the semiconductor, silicon, in biological applications is known in the literature and is described, for example, in WO 97/06101. Here it is disclosed that certain forms of porous silicon, in particular mesoporous silicon, are resorbable and dissolve over a period of time when immersed in simulated body fluid solution.

To date, the majority of studies relating to impregnation of porous silicon has been in the field of optoelectronic devices and structures. For example porous silicon has been impregnated with conductive material to improve the efficiency of light emitting diodes. Materials that have been incorporated into porous silicon include metals such as nickel, copper, iron, silver, and gold; semiconductors such as germanium, cadmium telluride, zinc selenide, and tin oxide; and polymers such as polypyrrole, polyaniline, polystyrene, and polymethylmethacrylate (PMMA).

As discussed by Herino in Properties of Porous Silicon EMIS Data Review Series, No 18, p 66 to 76 (1997), it has proved difficult to incorporate high concentrations of impregnated substance into relatively large volumes of porous silicon due to blocking of the narrow pores. Deposition of material towards the opening of the pores tends to prevent a high proportion of the material from occupying the pore system.

Zangooie et al in Thin Solid Films 313/4, p 825-830 (1998) report the adsorption of proteins in thin oxidised porous silicon layers. Spectrosopic ellipsometry was used to estimate protein incorporation in the porous silicon, the incorporation process resulting in a change in refractive index of the porous silicon. A volume percentage of adsorbed albumin of 10.7% was reported for 55% porous silicon. The subsequent release of protein was not demonstrated.

Studies on the deposition of solutions of compounds, including small drug molecules, peptides, glycolipids, and carbohydrates, ranging in size from 150 to 12,000 daltons, onto a mesoporous silicon sample surface using a desorption—ionisation technique are reported Wei in Nature (Vol 399, 243-246 (1999)). The concentrations used were extremely low (0.001 to 10 micromolar) and the depth of the penetration of the analytes was not recorded.

High levels of pore filling by germanium, another electronic material, are described by Halimaoui et al in J. Appl. Phys. 78, 3428-30 (1995). However, this involved the use of ultra high vacuum continuous vapour deposition, a technique which would not be suitable for most pharmaceutical applications.

It has been suggested that the properties of porous silicon render it useful as a vehicle for delivering beneficial substances to a subject. Where resorbable porous silicon is associated with a beneficial substance, for example, then resorption of the porous silicon in the body may result in release of the beneficial substance, affording the possibility of controlled release of the beneficial substance disposed in the pores of the porous silicon as a result of corrosion or dissolution of the resorbable silicon. Included within the literature are suggested applications in which the porous silicon is in the form of an implant impregnated with a beneficial substance (as described in WO 99/53898), a tablet or suppository (see, for example WO 01/29529) or alternatively is formulated into a particulate product associated with a beneficial substance for injection through the skin (see WO 01/76564) or for delivery as a dermatological or pulmonary formulation (as described in WO 02/15863 and WO 03/011251 respectively).

Although the potential for using microparticles of porous silicon as a delivery vehicle for a beneficial substance has been mentioned, high loading levels of beneficial substance, especially where the beneficial substance is an organic compound, remain difficult to achieve and no such compositions have been exemplified previously.

WO 03/011251, mentioned above, implies that a desired loading level may be achieved by a process of incubating porous silicon in a solution of the active agent (such that the solution of the active agent penetrates into the pores of the porous silicon by capillary action) and then removing the solvent. In practice, however, this method is generally less suitable for situations where it is required that the beneficial substance is delivered at high doses.

WO 99/53898 discusses the desirability of being able to deliver beneficial substances by means of a silicon implant but states that restrictions on the physical size of the drug payload for implants restricts their use, in practical terms, to delivering microminerals or other substances which are not required at high levels. Loading of porous silicon implants with various metals or compounds of metals by a method involving melting a salt of the metal on the surface of a sample of porous silicon is demonstrated but it is suggested that such a method would not be applicable in the case of large organic drug molecules as thermal degradation would be expected to occur when melting takes place. There would be no motivation, therefore, to look to the method of WO 99/53898 for the delivery of high doses of beneficial organic compounds.

The combination of silicon microparticles with a cytotoxic agent such as 5-fluorouracil is mentioned in WO 02/067998 but there is no disclosure of high loading levels. Moreover, although a number of possible ways of associating the cytotoxic agent with the microparticles are discussed, there is no suggestion that methods involving heating would be appropriate.

There therefore remains a continuing need for the development of improved dosage forms for the controlled release of beneficial organic substances, especially for use in situations where the organic substance is required to be delivered at high doses.

SUMMARY OF THE INVENTION

The present inventors have surprisingly found that porous silicon may be loaded with high levels of beneficial organic substance throughout substantially the entire porous material without the organic substance becoming significantly degraded, thereby affording the possibility that high doses of beneficial organic substance can be delivered over a period of time and in a controlled manner. Composite materials comprising porous semiconductor impregnated with a substantially uniformly distributed high loading of beneficial organic substance may therefore suitably be formulated as pharmaceutical implants for controlled release or more particularly unexpectedly advantageously can be prepared in the form of microparticles and injected into the target site using a fine needle.

According to a first aspect, therefore, the present invention provides a composite material comprising a porous semiconductor impregnated with at least one beneficial organic substance, wherein the beneficial organic substance is present in an amount of at least 15% by weight, based on the weight of the material.

Also provided, according to further aspects, is the use of such a material in therapy and a pharmaceutical composition for the delivery of a beneficial organic substance to a patient comprising such a material.

In a further aspect, the invention provides a method of delivering a beneficial substance to a patient in need thereof comprising delivering to the patient a composition as described above and the use of a porous semiconductor in such a method.

The invention also provides a method for preparing a composite material comprising a porous semiconductor impregnated with at least one beneficial organic substance, wherein the beneficial organic substance is present in an amount of at least 15% by weight based on the weight of the composite material, comprising the steps of:—
  i) bringing the beneficial organic substance into contact with the porous semiconductor; and
  ii) allowing the beneficial organic substance to impregnate the porous semiconductor, the impregnation being performed at a temperature which is at or above the melting point of the beneficial organic substance.

Also provided is a method for preparing a composite material comprising a porous semiconductor impregnated with at least one beneficial organic substance, wherein the beneficial organic substance is present in an amount of at least 15% by weight based on the weight of the composite material, comprising the steps of:—
  i) dissolving the beneficial organic substance in a solvent for the beneficial organic substance;
  ii) bringing the solution of part(i) into contact with the porous semiconductor; and
  iii) allowing the beneficial substance to impregnate the porous semiconductor, the impregnation being performed at a temperature in the range of from 40° C. to 200° C.

By means of the invention, composite porous semiconductor materials with high organic substance loading distributed with high uniformity throughout substantially the entire porous material are provided. The method of introducing the beneficial substance into the porous semiconductor allows for a high proportion of the beneficial substance to occupy the pore volume and so the resulting materials have low porosity (due to the high pore filling).

The use of composite materials having a high loading of beneficial organic substance with a high level of pore filling to prepare pharmaceutical compositions is advantageous in commercial terms as it means that fewer raw materials are required; not only is it possible to administer the composition fewer times in order to deliver the desired dose of beneficial substance but also the high pore filling levels mean that high loading can be achieved with very little of the beneficial substance being wasted.

Particularly advantageously, composite porous semiconductor materials according to the present invention may be used to deliver high doses of poorly water soluble or hydrophobic organic compounds. The dissolution rate of the drug into aqueous bodily fluids following administration impacts on the bioavailabilty of the drug and so compounds which have low aqueous solubility tend to be poorly bioavailable following administration, leading to difficulties in rapidly attaining therapeutically effective drug levels. This represents a significant problem in the development of pharmaceutical compositions containing such active ingredients. By providing the beneficial organic substance in porous matrix form according to the present invention, however, the surface area of the organic substance available to contact the aqueous media at the site of administration or site of absorption is maximized, thereby enhancing its dissolution rate and hence the bioavailability.

DETAILED DESCRIPTION OF THE INVENTION

As used herein, the term 'beneficial substance' refers to any organic substance used in therapy or diagnosis which has an overall beneficial effect upon the patient to which it is administered. Included within this term are substances that may be, to some extent, toxic to the patient provided that the overall effect upon the patient is beneficial, for example the substance may be a toxin or toxic to undesirable cells or may interfere with an undesirable physiological process but would still be considered 'beneficial' overall.

By 'organic' is meant that the beneficial substance comprises molecules having a skeleton of carbon atoms.

The term 'patient' means a human or animal to which the beneficial substance is to be administered.

The porous semiconductor may suitably be doped or undoped. Suitable semiconductors for use according to the invention include silicon carbide, silicon nitride and germanium but preferably the semiconductor is silicon.

Porous silicon may be classified depending upon the nature of the porosity (the porosity is the fractional void content by volume). Microporous silicon has an average pore size of less than 2 nm, mesoporous silicon has an average pore size between 2 and 50 nm and macroporous silicon contains pores having a diameter greater than 50 nm. As described in WO 97/06101, mentioned above, certain forms of porous silicon have been found to be resorbable. 'Resorbable' relates to material that will dissolve at normal physiological temperatures (37° C.±1° C.) in simulated body fluid over a period of time, for example of up to 8 weeks and generally at less than 2 weeks. Simulated body fluid may comprise a solution of reagent grade salts in deionised water so that the ionic concentration reflects that found in human plasma or alternatively it may comprise a simulated synovial fluid, sweat or other body fluids.

Porous silicon may comprise partially oxidized porous silicon, that is, porous silicon that has been oxidized in such a manner that part of the porous silicon remains completely unoxidised.

For use according to the present invention, the porous silicon may be microporous, mesoporous or macroporous. It will be appreciated that the nature of the porosity of the porous silicon used according to the invention will depend on the intended mode of delivery and the size and properties of the beneficial organic substance with which it is loaded, among other things but preferably the porous silicon is mesoporous.

Preferably, the porous silicon for use according to the invention has a porosity prior to loading of between 1% and 99%, preferably between 20% and 90%, especially between 40% and 90%.

The porous silicon preferably comprises resorbable porous silicon.

For a given silicon skeleton size distribution, the higher the porosity of the porous silicon, the faster it is resorbed, Depending on the choice of pore size, pore density and total volume of pore to skeleton in the porous silicon, therefore, it is possible to produce compositions which may be resorbed faster or slower, as required.

The silicon may be pure silicon or it may be doped, for example with boron. Silicon wafers are classified depending on the level of doping with either p− or p+, with p− wafers having relatively low levels of boron doping and p+ wafers having higher levels of boron doping (with resistivities in the order of 0.005 ohm.cm$^{-1}$). In the present invention, the silicon used is preferably derived from p+ silicon.

The porous semiconductor for use according to the invention may comprise a single sample of porous silicon (in which any part of the porous silicon is substantially integral with the remaining parts of the sample), suitably of thickness between 100 nm and 1 mm, preferably between 1 micron and 750 microns.

Alternatively, the porous semiconductor may be in particulate form, comprising at least one porous semiconductor particle. Preferably the composition according to the invention comprises a multiplicity of porous semiconductor particles have a mean particle size of between 100 nm to 10 microns, preferably 500 nm to 2 microns. The multiplicity of porous semiconductor particles preferably comprises a multiplicity of particles having the same shape and more preferably also the same volume as each other. The particles are each preferably substantially symmetrical and may be substantially oval, spherical or in the form of microneedles.

Porous silicon particles for use in the invention may be prepared by a number of known techniques. For example, a single crystal wafer silicon may be porosified by anodisation, for example, using HF and an electric potential. Alternatively, microparticles derived from polycrystalline feed stock may be manufactured by a two stage process, firstly by jet-milling the particle size from a few millimeters to a uniform micron sized stock followed by stain etching through established methods.

It will be appreciated that the porous semiconductor may be formed into an implantable implant or made into particulate form either prior to or after loading with the beneficial substance.

The beneficial organic substance for use according to the invention may be any pharmaceutically or diagnostically useful organic compound which has a beneficial effect when administered to a patient. Typically, the beneficial organic substance is an organic compound having a carbon atom skeleton comprising at least 5 carbon atoms, preferably at least 10 carbon atoms and may suitably be selected from one or more pharmaceutical compounds or biological materials such as antibodies, peptides and genetic constructs. Particular examples include antidepressants, anti-inflammatory agents, anaesthetics, anthelminthics, antioxidants and anticancer compounds, including cytotoxic compounds such as alkylating agents, cytotoxic antibodies, antimetabolites, alkaloids and hormonal regulators.

As discussed above, the present inventors have found that compositions according to the invention may advantageously be used to deliver high doses of compounds with poor solubility and low bioavailability.

Thus, according to one preferred embodiment, the organic substance is a pharmaceutical compound of low aqueous solubility, that is it has a solubility of no more than 10 mg/mL in aqueous media at normal physiological temperatures and pH range 1-7. Classes of drug with examples that fall into this category include antihypertensives, antianxiety agents, anticancer agentsanticlotting agents, anticonvulsants, blood glucose lowering agents, decongestants, antihistamines, antiussives, antineioplastics, beta blockers, anti inflammatories, antipsychotic agents, cognitive enhancers, cholesterol reducing agents, anti-atherosclerotic agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors and cholesterol ester transfer protein inhibitors.

High levels of loading of beneficial organic substance may be achieved by performing the impregnation at an elevated temperature, particularly at a temperature which is at or above the melting point of the beneficial organic substance. It will be appreciated that in order to minimize the possibility of thermal degradation occurring, it is therefore preferable that the beneficial substance has a low melting point.

Accordingly, in another embodiment, the beneficial organic substance is suitably a pharmaceutical compound which has a melting point of below 300° C., more preferably below 200° C., even more preferably below 100° C. Examples include pilocarpine (m.p. 34° C.), ephedrine (m.p. 38-43° C.), cyclophosphamide (m.p. 49-53° C.), procaine (m.p. 61° C.), chlorambucil (m.p. 64-69° C.), lignocaine (m.p. 66-69° C.), ibuprofen (m.p. 75-78° C.) plumbagin (m.p. 78-79° C.), flurazepam (m.p. 77-82° C.), fentanyl histamine (m.p. 83-84° C.), busulfan (m.p. 114° C.), lauric acid (m.p. 44° C.), amitriptyline HCl (m.p. 198-200° C.), rifampicin (m.p. 183-188° C.), medoxyprogesteron acetate (m.p. 271° C.), paclitaxel (m.p. 216-217° C.), levasimole (m.p. 227-233° C.) and dexamethasone (m.p. 250-253° C.).

Particular beneficial organic substances suitable for use according to the present invention include chlorambucil, amitriptyline, ibuprofen, procaine, levamisole, plumbagin, cyclophosphamide, busulfan, dexamethasone, lauric acid, rifampicin, medroxyprogesteron acetate and paclitaxel. In a particularly preferred embodiment, the beneficial organic substance is chlorambucil or paclitaxel.

It will, of course, be appreciated that the porous semiconductor may have more than one beneficial organic substance incorporated within its structure. Unless otherwise indicated, reference to 'beneficial organic substance' should therefore be understood accordingly.

In the composite materials according to the invention, the porous semiconductor is impregnated with at least 15% by weight of beneficial organic substance, based on the weight of the composition. Preferably the beneficial organic substance is present in an amount of from 15% to 85% by weight, particularly from 20% to 50% by weight, especially from 30% to 40% by weight, based on the weight of the composition It will be appreciated that the high loading levels by weight of the materials according to the invention equate to a high percentage by volume of the pores in the porous semiconductor being occupied by the beneficial substance. The percentage of the maximum loading capacity that is occupied by the beneficial substance (that is, the % of the total volume of the pores in the porous semiconductor that is occupied by beneficial substance) for materials according to the invention is typically in the range of from 30% to 100%, especially from 50% to 90%. For any given composite material, this value can be determined by dividing the volume of beneficial substance taken up during loading (equivalent to the mass of substance taken up divided by its density) by the void volume of the porous semiconductor prior to loading, multiplied by a hundred.

In the composite material according to the invention the beneficial substance is distributed substantially uniformly throughout the pores of the semiconductor carrier material by which is meant that the porous semiconductor is impregnated with beneficial organic substance in an amount of from 15% to 85%, more preferably from 20% to 50%, especially from 30% to 45% by weight (based on the weight of the material) to a pore depth from the surface of the material of at least 50 microns, preferably at least 100 microns, especially at least 150 microns.

Quantification of gross loading may conveniently be achieved by a number of known analytical methods, including gravimetric, EDX (energy-dispersive analysis by x-rays), Fourier transform infra-red (FTIR) or Raman spectroscopy of the pharmaceutical composition or by UV spectrophotometry, titrimetric analysis, HPLC or mass spectroscopy of the eluted beneficial substance in solution. Quantification of the uniformity of loading is achievable by compositional techniques that are capable of spatial resolution such as cross-sectional EDX, Auger depth profiling, micro-Raman and micro-FTIR.

Reference to the surface of the material is to the surface that separates the sample of porous semiconductor from its surroundings.

In the composite material according to the invention, the beneficial substance is incorporated and released from the semiconductor carrier material without significant degradation.

Pharmaceutical compositions according to the invention may conveniently be presented for use in conventional manner in admixture with one or more pharmaceutically acceptable excipients. The compositions may be formulated for administration in any suitable manner, typically in the form of an implant, suitably for subcutaneous, intramuscular, intraperitoneal or epidermal introduction or for implantation into an organ (such as the liver, lung or kidney). Alternatively, compositions according to the invention may be formulated for parenteral administration in the form of an injection (for example, intravenously, intravascular, subcutaneous, intramuscular or infusion), or for oral administration.

A porous semiconductor material impregnated with at least one beneficial organic substance wherein the beneficial organic substance is present in an amount of at least 15% by weight based on the composite material may be prepared by a method comprising the steps of:— i) bringing the beneficial organic substance into contact with the porous semiconductor; and ii) allowing the beneficial organic substance to impregnate the porous semiconductor, the impregnation being performed at a temperature which is at or above the melting point of the beneficial organic substance.

Preferably, the impregnation is performed at a temperature in the range of from 40° C. to 200° C., especially at a temperature of from 60° C. to 130° C.

This may be achieved by a method comprising the steps of:— i) heating the porous semiconductor to a temperature at or above the melting point of the beneficial organic substance;

ii) bringing the beneficial organic substance into contact with the heated porous semiconductor, thereby causing the beneficial organic substance to become molten; and iii) allowing the molten beneficial organic substance to impregnate the porous semiconductor.

Alternatively, the impregnation may be brought about by the steps of:— i) heating the beneficial organic substance to a temperature at or above its melting point, thereby causing the beneficial organic substance to become molten;

ii) bringing the molten beneficial organic substance into contact with the porous semiconductor; and iii) allowing the molten beneficial organic substance to impregnate the porous semiconductor.

In a yet further embodiment, both the porous semiconductor and the beneficial organic substance may be heated independently to a temperature at or above the melting point of the beneficial organic substance and then brought into contact together to allow impregnation to occur.

Preferably, the porous semiconductor is pre-heated before introduction of the beneficial organic substance. This helps to remove physisorbed moisture within the pores also has the effect of causing the matrix to expand such that it can more effectively incorporate the beneficial substance. Conveniently, this pre-heating may be achieved by heating the porous semiconductor to a temperature in the range of from 100° C. to 250° C. for a period of from 5 to 15 minutes.

In order to facilitate impregnation of the porous semiconductor by the molten beneficial organic substance, the temperature at which the impregnation is performed may be any temperature at or above the melting point of the beneficial organic substance, conveniently at a temperature which is from 5° C. to 15° C. above the melting point of the beneficial organic substance.

Where the porous semiconductor has been pre-heated to remove moisture from the pores, it will be appreciated that it may be necessary to cool the pre-heated porous semiconductor down to the desired temperature prior to bringing it into contact with the beneficial organic substance.

The time during which the beneficial organic substance and the porous semiconductor are maintained in contact together at elevated temperature should be sufficient to allow impregnation to occur. Conveniently, this is for a period of from 1 minute to 2 hours, typically 5 minutes to 1 hour Following impregnation by the beneficial organic substance, the treated porous semiconductor may conveniently be washed with a suitable solvent for the beneficial substance concerned, in order to remove any excess beneficial substance on the surface. It will be appreciated that the choice of solvent will depend on the beneficial organic substance concerned; any solvent suitable for the beneficial substance known in the art, or mixtures thereof, may be used. Conveniently, the solvent is an organic solvent or an aqueous organic solvent, preferably an alcohol, especially ethanol or a mixture of ethanol and water Not only is it unexpected that a loading technique involving a melting step would be successful for organic compounds (which would be expected to exhibit thermal degradation) but it would also be expected that the molten (and therefore more viscous) beneficial substance would tend to lead to blocking of the pores in the porous semiconductor, preventing a large proportion of the pore volume from being occupied and hence limiting the loading levels achievable. The finding that high loading levels of organic substance can be achieved using this method is therefore surprising.

Chlorambucil is known to be particularly sensitive to thermal degradation and has been reported to have an apparent activation energy for thermal degradation (Ea) in an aqueous environment of 24.4 kcal/mol (J. Pharm Sci, 69, 1091-1094 (1980)). This lies at the high end of the range (10 to 30 kcal/mol) for most drugs. It is therefore particularly surprising that in the case of chlorambucil, a method involving melting the beneficial substance would give high loading levels without significant degradation occurring.

Melting the beneficial substance directly onto the heated porous semiconductor in accordance with the above method reduces the number of process steps involved and minimises the risks of introducing undesirable contaminants. Despite these advantages, however, the present inventors have found that it can be beneficial to dissolve the beneficial substance in a suitable solvent prior to contacting it with the porous semiconductor in the impregnation step, because solutions tend to be easier to handle, especially where only small quantities are involved, leading to advantages in processability. This method can also be applied to beneficial organic substances which cannot be heated to their melting temperatures without suffering substantial degradation, and to beneficial organic substances where the molten material is too viscous to allow efficient incorporation into the porous structure.

According to a further aspect, therefore, the impregnation is performed by a method comprising the steps of:— i) dissolving the beneficial organic substance in a solvent for the beneficial organic substance;
ii) bringing the solution of part(i) into contact with the porous semiconductor; and
iii) allowing the beneficial substance to impregnate the porous semiconductor, the impregnation being performed at a temperature in the range of from 40° C. to 200° C.

Preferably, the impregnation is performed at a temperature of at least 60° C., especially in the range of from 60° C. to 130° C.

In a particular embodiment, the impregnation is performed at a temperature which is at or above the boiling point of the solvent in which the beneficial organic substance is dissolved. For example, a temperature of around 90° C. is suitable when ethanol is the solvent.

In another preferred embodiment, the chosen temperature should be at or above the melting point of the beneficial organic substance, provided that degradation does not occur to a significant extent at that temperature.

It is particularly preferred that the temperature chosen is at or above the boiling point of the solvent in which the beneficial organic substance is dissolved but is also at or above the melting point of the beneficial organic substance, provided that degradation does not occur to a significant extent at that temperature.

In this aspect, impregnation may be brought about by a method comprising the steps of:— i) dissolving the beneficial organic substance in a solvent for the beneficial organic substance;
ii) heating the porous semiconductor to the temperature at which impregnation is to be performed;
iii) bringing the solution of part(i) into contact with the heated porous semiconductor; and
(iv) allowing the beneficial substance to impregnate the porous semiconductor Alternatively, the impregnation may be brought about by the steps of:— i) dissolving the beneficial organic substance in a solvent for the beneficial organic substance;
ii) heating the solution of part(i) to the temperature at which impregnation is to be performed;
iii) bringing the heated solution of part(ii) into contact with the porous semiconductor; and
(iv) allowing the beneficial substance to impregnate the porous semiconductor In a yet further embodiment, both the porous semiconductor and the solution of beneficial organic substance may be heated independently to the temperature at which impregnation is to be performed and then brought into contact together to allow impregnation to occur.

Suitable process conditions for bringing the beneficial organic substance and porous semiconductor into contact to allow impregnation to occur are as described above. Any solvent suitable for the beneficial substance known in the art, or mixtures thereof, may be used. Conveniently, the solvent is an organic solvent or an aqueous organic solvent, preferably an alcohol, especially ethanol or a mixture of ethanol and water.

The optional additional steps of pre-heating of the porous semiconductor in order to remove moisture prior to introducing the beneficial substance and/or washing of the treated porous semiconductor following the introduction of the beneficial substance as described above may preferably be performed.

In a yet further aspect, where the beneficial organic substance is a liquid at room temperature (such as vitamin E, vitamin K), the impregnation may be brought about by the steps of heating the liquid beneficial organic substance to a temperature in the range of from 40° C. to 200° C., bringing the heated liquid into contact with the porous semiconductor and allowing the beneficial substance to impregnate the porous semiconductor.

Alternatively the impregnation may be brought about by heating the porous semiconductor to a temperature between 40° C. and 200° C., bringing the liquid beneficial organic substance into contact with the heated porous semiconductor and allowing the beneficial substance to impregnate the porous semiconductor.

In a further embodiment, both the porous semiconductor and the liquid beneficial organic substance are heated to a temperature of between 40° C. and 200° C., then the liquid beneficial substance is brought into contact with the porous semiconductor and the beneficial substance is allowed to impregnate the porous semiconductor.

Preferably, the impregnation of porous semiconductor with the liquid beneficial substance is carried out at a temperature within the range of from 60° C. to 130° C.

The optional additional steps of pre-heating of the porous semiconductor in order to remove moisture prior to introducing the beneficial substance and/or washing of the treated porous semiconductor following the introduction of the beneficial substance as described above may preferably be performed The invention may be further illustrated by the following non-limiting examples, when read together with the accompanying figures in which:—

FIG. 1 shows a scanning electron micrograph along the cross-sectional view of an unimpregnated porous silicon p+ membrane (pSi/p+). With reference to the total thickness of the membrane (~160 μm), Top refers to EDX positioned at 1-5 μm from the polished side of membrane Mid. Top is referred to 35-45 μm from the polished side of membrane Middle is referred to 75-85 μm in between unpolished and polished side of membrane Mid. Bottom is referred to 35-45 μm from the unpolished side of membrane Bottom is referred to EDX positioned at 1-5 μm from the unpolished side of membrane.

The polished side of the membrane refers to the original highly polished face of the wafer, prior to porosification.

| FIG. Nos. | Beneficial organic substance |
|---|---|
| 6 | Amitriptyline HCl |
| 7 | Ibuprofen |
| 8 | Procaine |
| 9 | Levamisole HCl |
| 10 | Plumbagin |
| 11 | Cyclophosphamide |
| 12 | Busulfan |
| 13 | Dexamethasone |
| 14 | Lauric acid |
| 15 | Vitamin E |
| 16 | Vitamin K |

Figure 17:
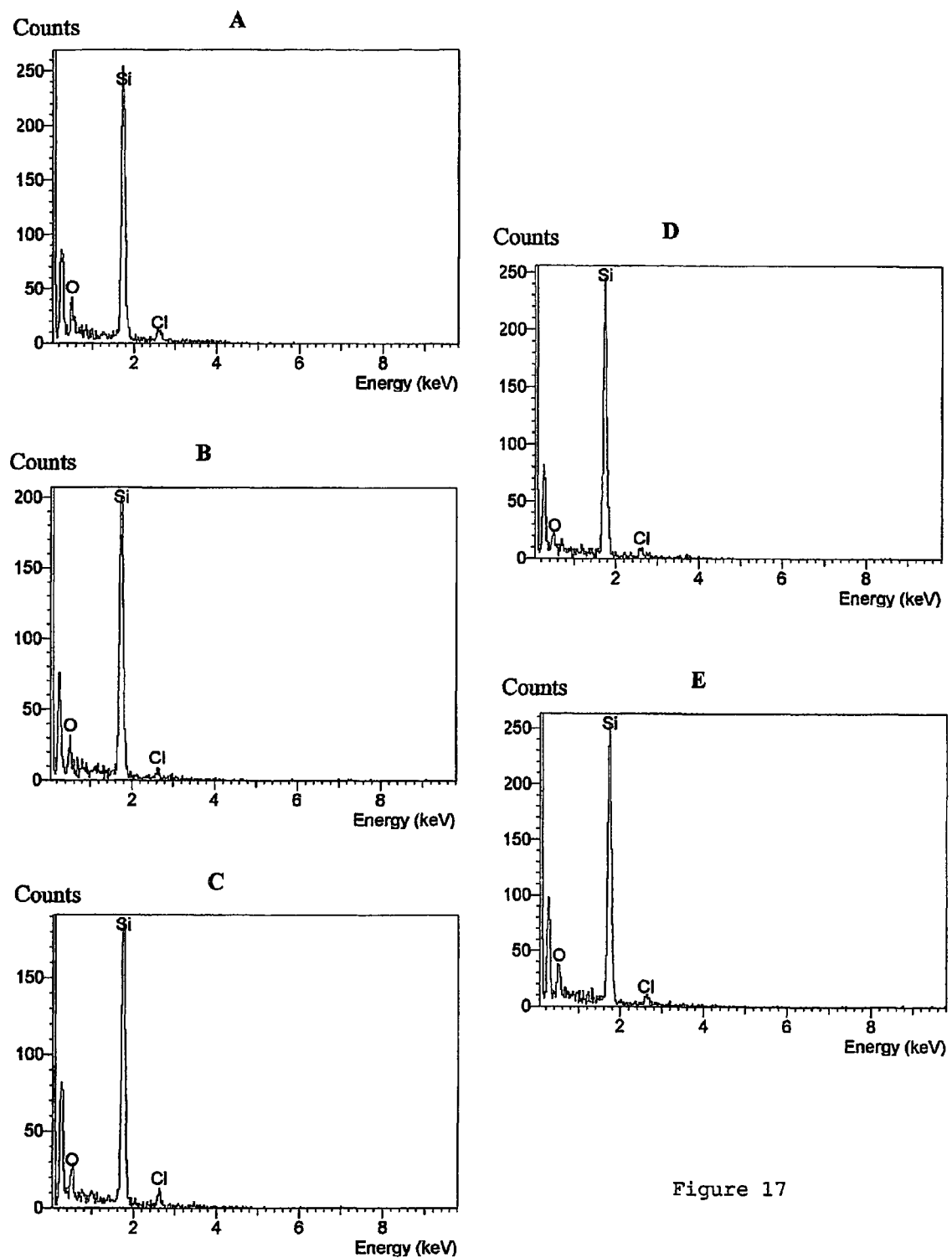

FIG. 17 shows the SEM-EDX analysis of a porous silicon p+ membrane impregnated with chlorambucil. Each EDX spectrum is labelled with the position of EDX performed on the cross-section of the membrane according to the definition of FIG. 1 that is A (Top), B (Mid Top), C (Middle), D (Mid Bottom), E (Bottom).

Figure 18:
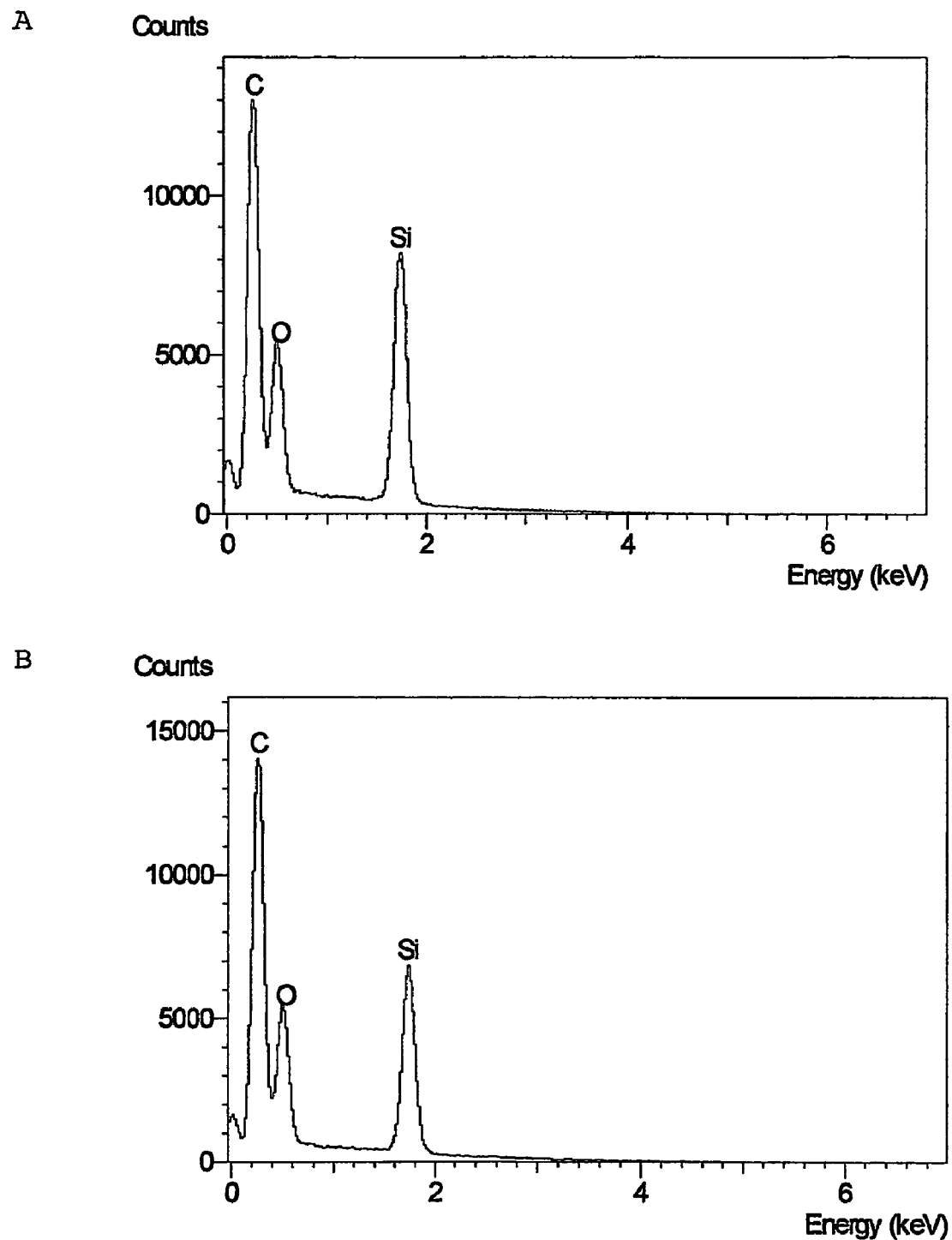

FIG. 18 shows the SEM-EDX analysis of a paclitaxel impregnated porous silicon/p+ membrane performed on the cross-section of the membrane at a depth of (A) 80 μm and (B) 145 μm from the surface of the material.

Figure 19:
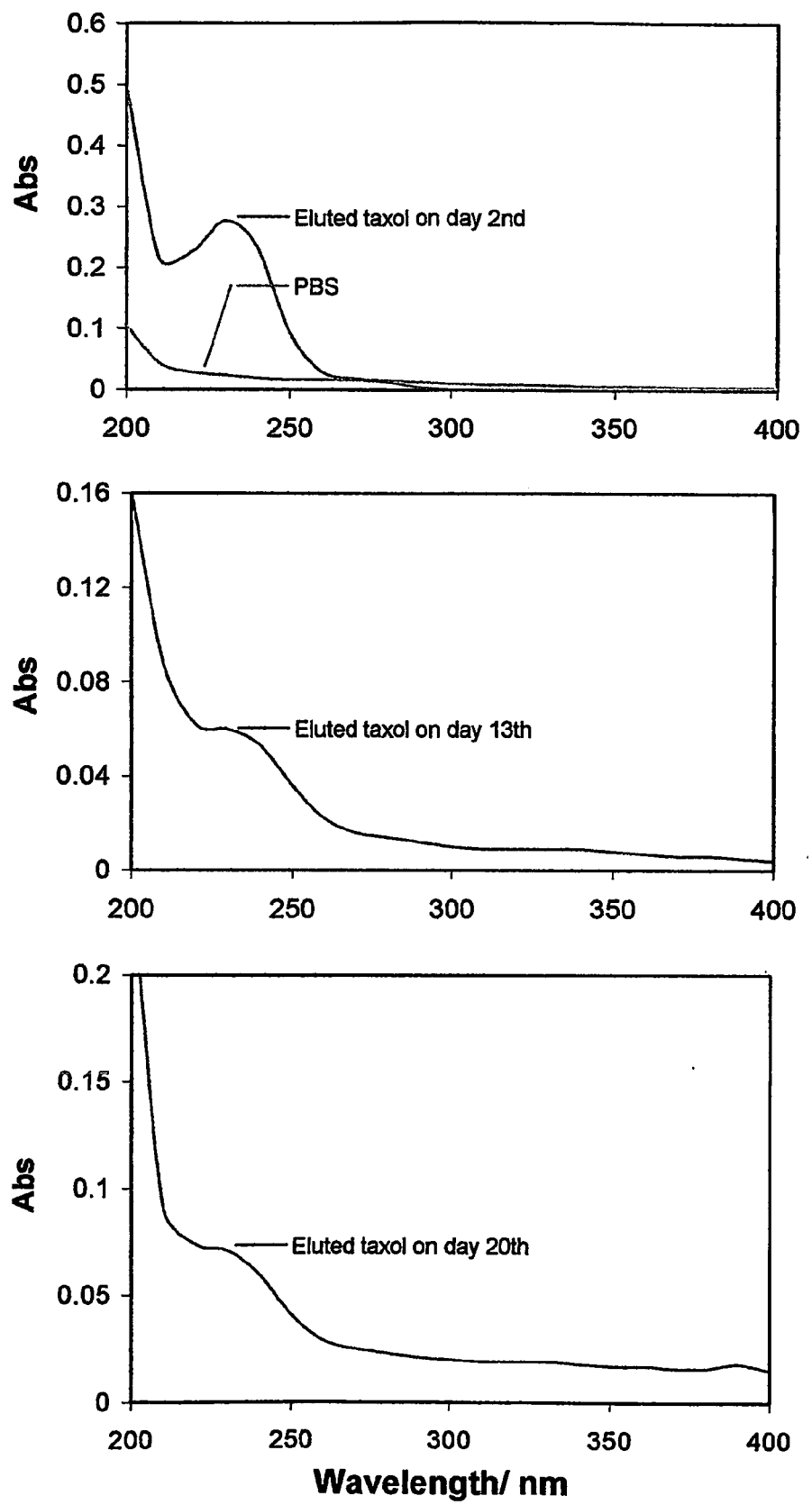

FIG. 19 shows the UV profiles obtained from PBS eluted samples of paclitaxel impregnated porous silicon membrane on days 2 (A), 13 (B) and 20 (C).

Figure 20:
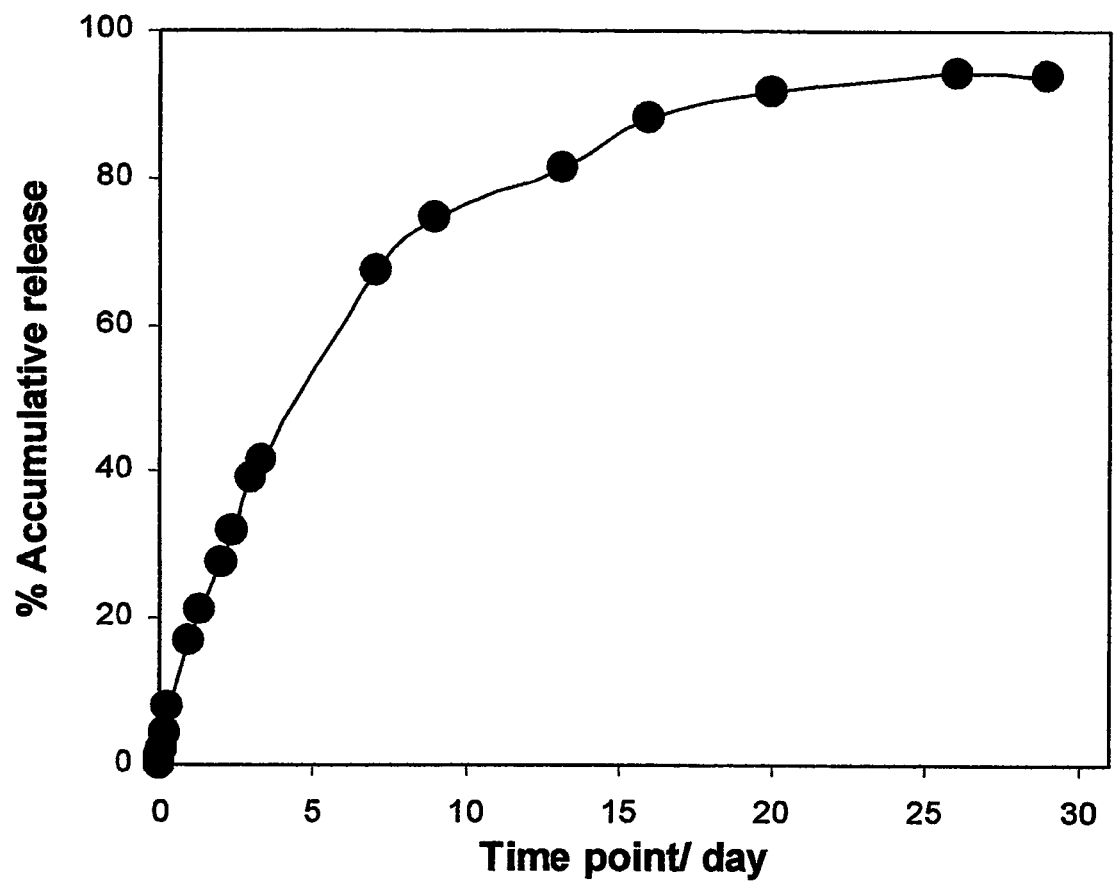

FIG. 20 shows the graph obtained for the cumulative release of paclitaxel from impregnated porous silicon membrane measured over a period of 30 days.

Figure 21:
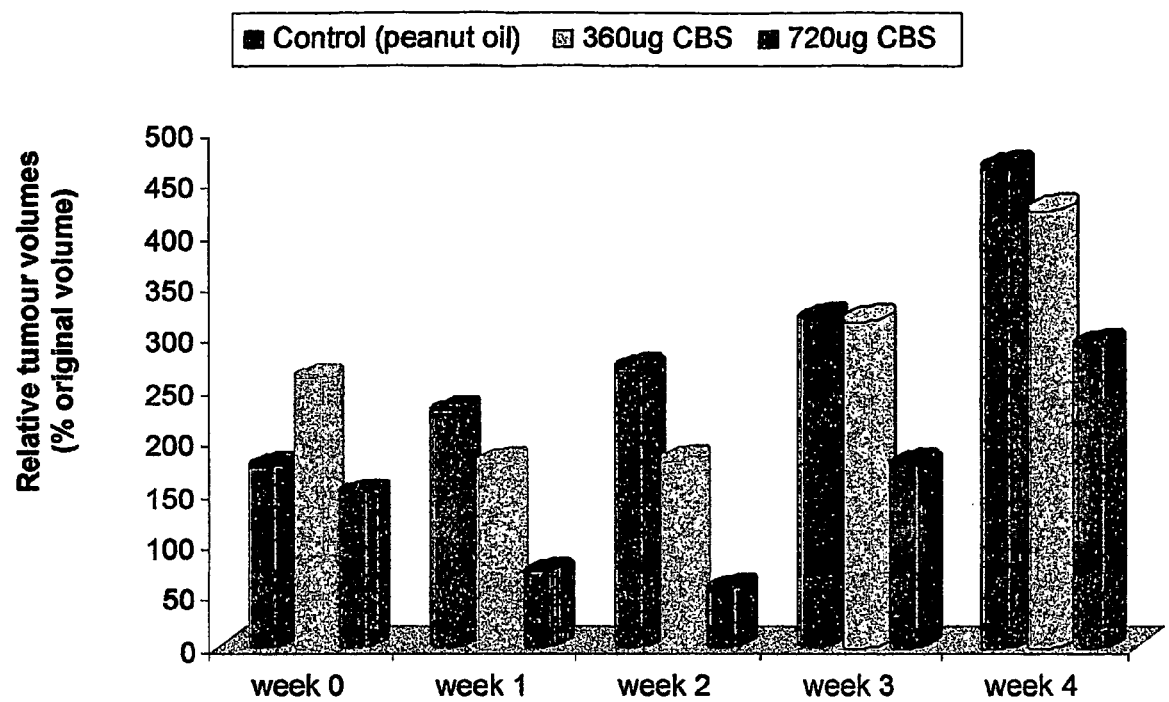

FIG. 21 shows the effects on tumour regression following intratumoural injection of two dosages of chlorambucil impregnated into porous silicon membrane (CBS). The control group received intratumour injection of 100 ul of peanut oil only.

Figure 22:
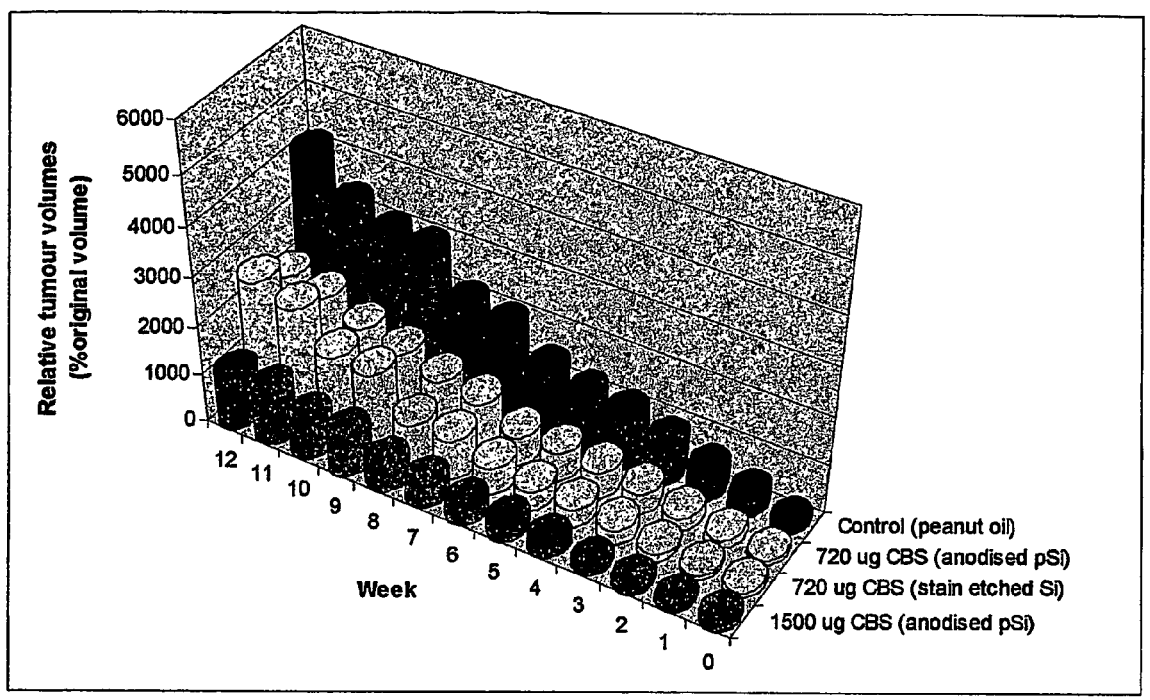

FIG. 22 shows the dose-dependent regression of human tumour in mice following intratumoural injection of chlorambucil delivered by porous silicon. (CBS). The control group received intratumour injection of 100 ul of peanut oil only.

Figure 23:
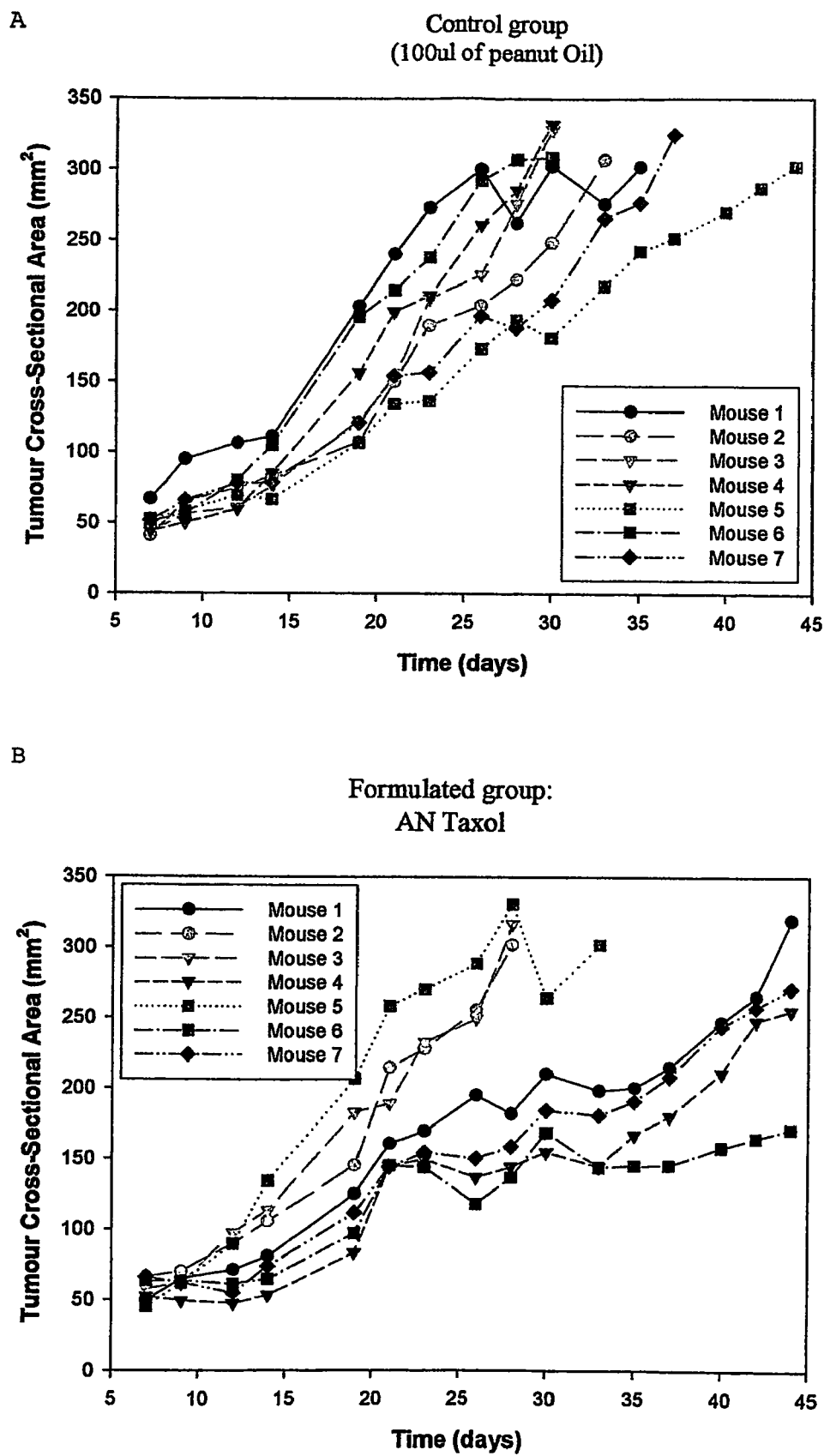

FIG. 23 shows the graphs obtained for tumour cross-sectional area over time in mice following intratumoural administration of peanut oil(A) and paclitaxel loaded porous silicon (B)

EXAMPLES

(a) Preparation of Impregnated Porous Silicon Membranes

Examples 1-15 below illustrate the preparation of porous silicon membranes impregnated with substantially uniformly distributed high loading of various beneficial organic substances.

The porous membranes were prepared and loaded with beneficial substance according to the following general method:—

A 3 inch diameter p+ wafer (5-15 milli ohm cm) was made mesoporous in a 50:50 by volume mixture of 40 wt % HF and ethanol by anodisation at 35 mA/cm$^2$ for 90 minutes. The current density was then increased to 117 mA/cm$^2$ for 20 seconds. During the subsequent ethanol rinse, the mesoporous film detaches from the underlying bulk silicon wafer as a fully intact membrane of weight 479.6 mg, thickness 162 microns and porosity 63%. The membrane was then broken into flakes of weight in the range 10-60 mg for gravimetric and EDX studies of beneficial substance incorporation.

Loading was performed on two similar porous silicon (p+) membranes.

Membrane 1

Weight = 479.60 mg

Porosity = 62.94%

Thickness = 161.73 μm

Anodizing weight loss = 814.75 mg $$\begin{aligned} \text{Total void volume} &= 814.75\,\text{mg}/\{\text{density of silicon}\} \\ &= 814.75\,\text{mg}/2.33\,\text{gcm}^{-3} \\ &= 0.3497\,\text{cm}^3 \end{aligned}$$

Membrane 2

Weight = 460.06 mg

Porosity = 64.07%

Thickness = 160.07 μm

Anodizing weight loss = 820.57 mg $$\begin{aligned} \text{Total void volume} &= 820.57\,\text{mg}/\{\text{density of silicon}\} \\ &= 820.57\,\text{mg}/2.33\,\text{gcm}^{-3} \\ &= 0.3522\,\text{cm}^3 \end{aligned}$$

The pore volume available in the porous silicon membrane that can be occupied by the drug is calculated as follows:

$$\begin{aligned} \text{Maximum loading capacity} = (\text{Void volume, cm}^3) \times \\ (\text{percentage of purity, \%}) \times (\text{density of drug, g cm}^{-3}) \end{aligned}$$

SEM-EDX was performed by the mean of JSM-6400 F Scanning Microscopy on the samples. A consistent accelerating voltage of 5 kV at pressure $10^{-6}$ mbar was used throughout the inspection.

Control Experiment

Figure 1:
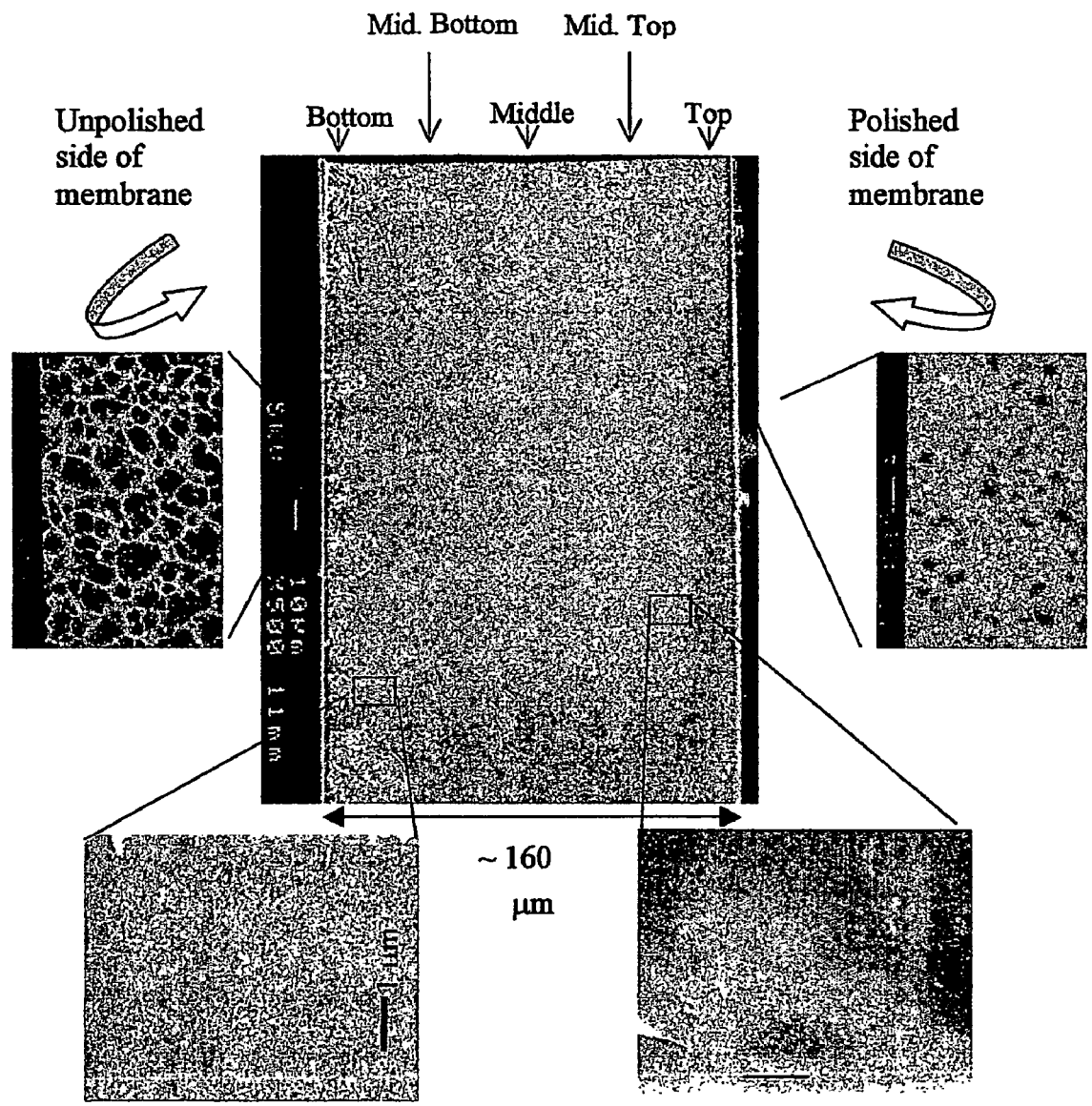
Figure 2:
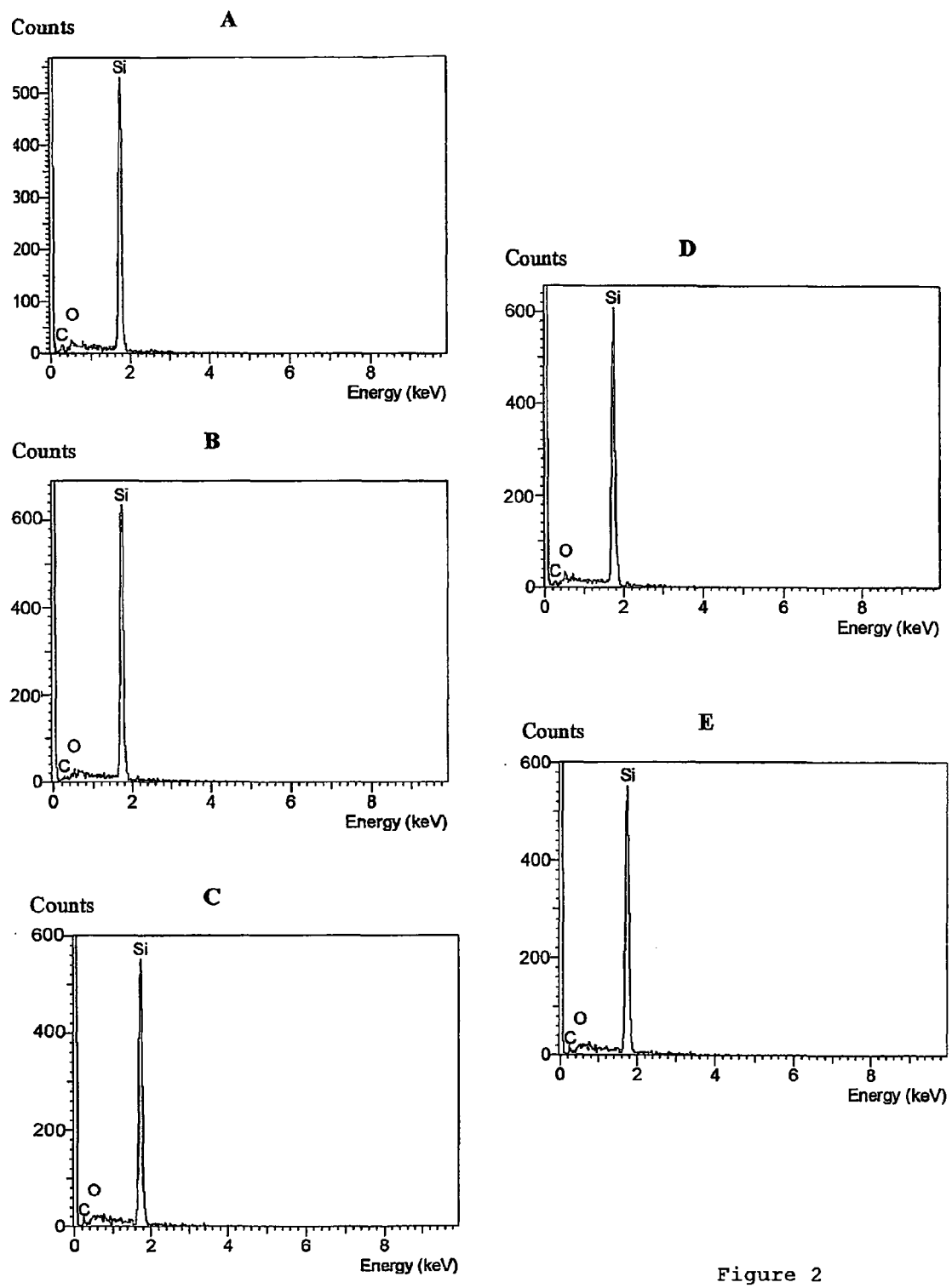
FIG. 2 shows the SEM-EDX analysis for an unimpregnated porous silicon p+ membrane. Each EDX spectrum is labelled with the position of EDX performed on the cross-section of the membrane as defined in FIG. 1, that is A (Top), B (Mid Top), C (Middle), D (Mid Bottom), E (Bottom).

SEM-EDX was conducted on the unloaded porous silicon/p+ membrane along its cross-sectional view (FIG. 1). Apart from the strong signal collected for Si, no significant contamination was detected. Only very small amounts of oxygen and carbon were observed (FIG. 2). The presence of oxygen could be attributed to the airborne atmospheric contamination and some native oxide formation. Very small carbon signals were detected on the surface (top or bottom) only, which could be due to the hydrocarbon contamination from the air.

Figure 3:
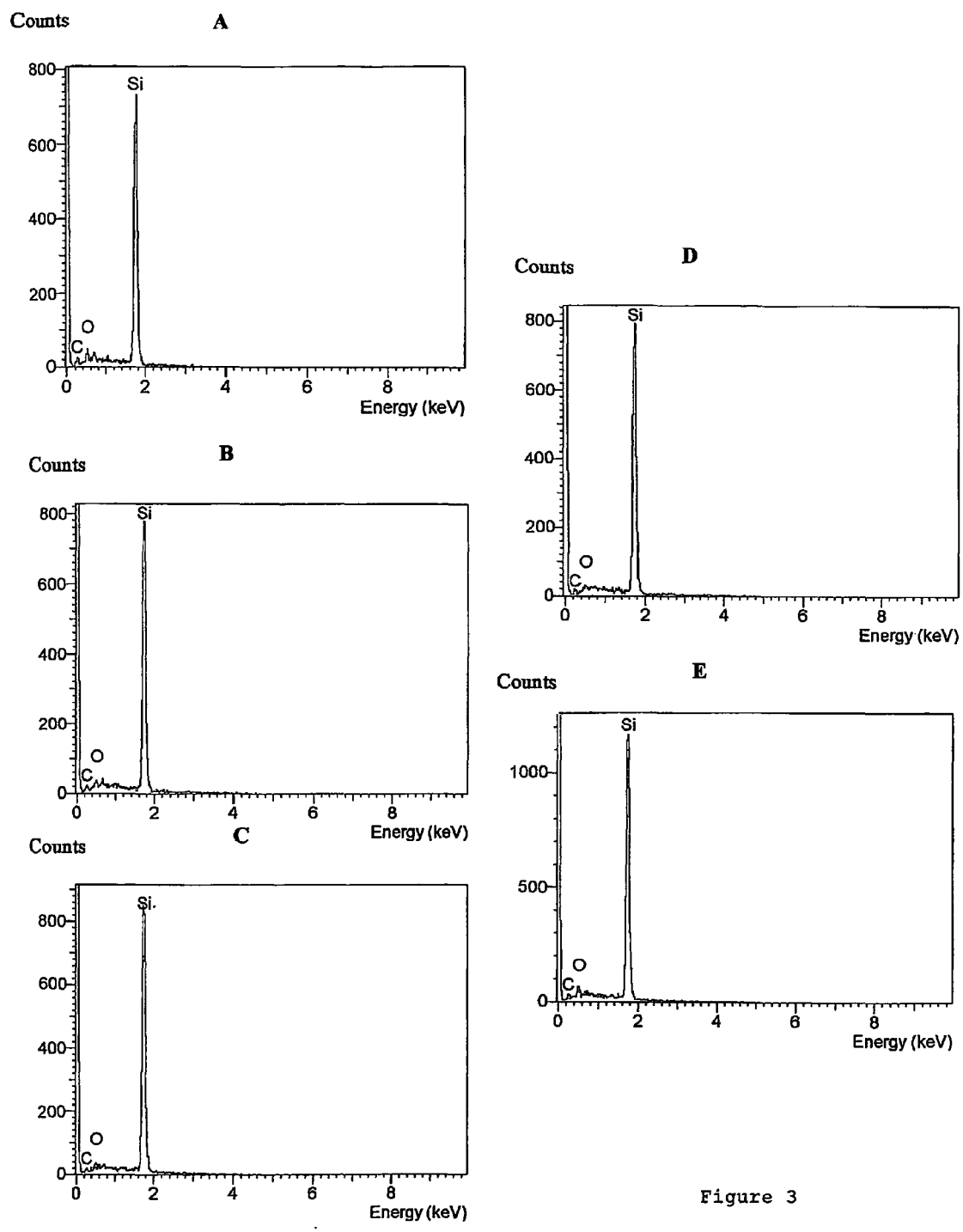
FIG. 3 shows the SEM-EDX analysis for an unimpregnated porous silicon p+ membrane when heated at 150° C. for 20 minutes with ethanol being pipetted onto its surface and undergoing evaporation. Each EDX spectrum is labelled with the position of EDX performed on the cross-section of the membrane according to the definition of FIG. 1.

A flake of membrane was heated at 150° C. for 20 minutes and pipetted with sufficient amount of ethanol as to serve the experimental control for the loading without drug. No significant amount of carbon or oxygen (derivable from the possible reaction between ethanol with porous silicon) is observed, suggesting that the ethanol (boiling point (78.3° C.) is completely evaporated under the applied heat without having the chance to react with porous silicon (FIG. 3).

1. Chlorambucil (Melting Point 64-66° C.)

Impregnation was performed using a direct impregnation-melting method with the applied heat ~10° C. above the melting point of chlorambucil at 80° C. for 25 minutes. After the drug loading and washing its weight increased to 72.92 mg equivalent to a w/w/loading of 39.19%. Thus the drug occupied 88.40/drug density of the pore volume available.

Weight of unloaded flake = 44.34 mg

Density = $d_{chl}$ g cm$^{-3}$ $$\begin{aligned} \text{Void Volume} &= \{44.34/479.60\,\text{mg}\} \times 814.75\,\text{mg}/\{\text{density of silicon}\} \\ &= 0.03233\,\text{cm}^3 \end{aligned}$$

$$\begin{aligned} \text{Maximum loading capacity} &= 0.03233\,\text{cm}^3 \times d_{chl}\,\text{g cm}^{-3} \\ &= 32.33\,d_{chl}\,\text{mg} \end{aligned}$$

Loading & washing $w_1 = 71.66$ mg $w_2 = 73.41$ mg $w_3 = 72.92$ mg equivalent to 39.19% w/w $$\begin{aligned} \% \text{ loading capacity } (w/v) &= \{72.92 - 44.34\}/\{32.33\,d_{chl}\} \times 100 \\ &= 88.40/d_{chl}\,\% \end{aligned}$$

Figure 4:
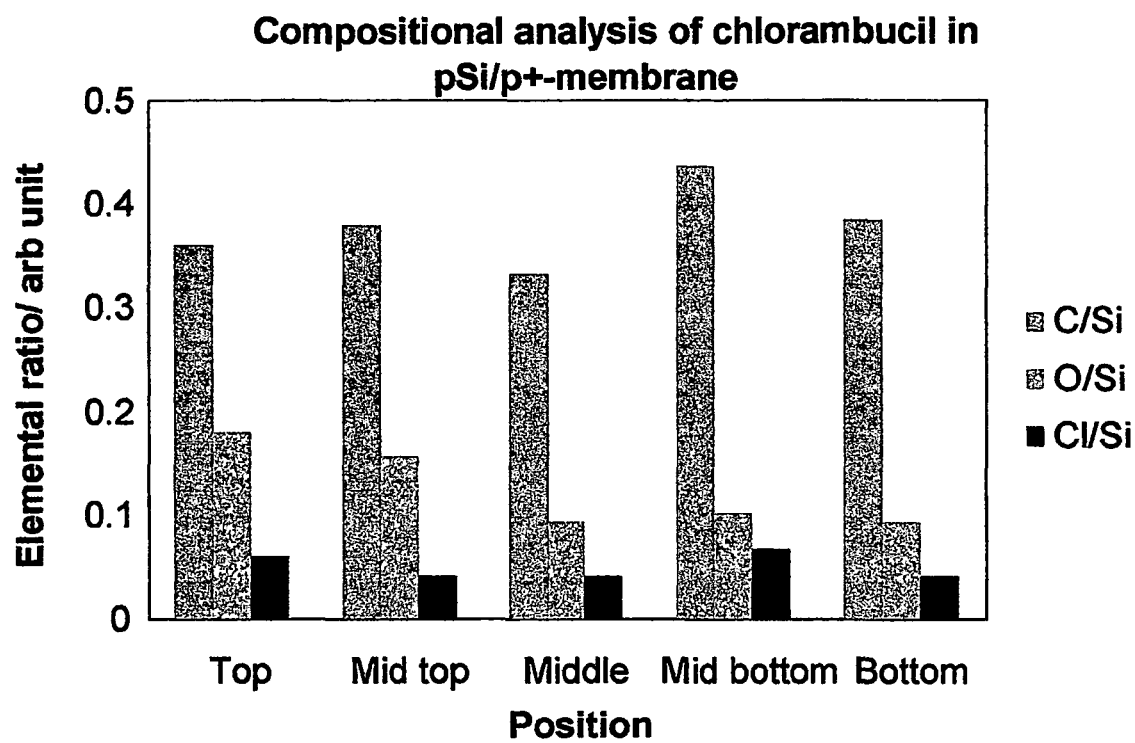
FIG. 4 shows the compositional analysis of a porous silicon p+ membrane impregnated with chlorambucil, as determined by SEM-EDX

Compositional analysis of the impregnated membrane, using the SEM-EDX method (FIG. 4), revealed that the loading of chlorambucil is fairly homogenous through the membrane, with reference to C/Si and Cl/Si ratios. High chlorambucil is detected, as evidenced with C/Si ~0.35 on average. The EDX spectra obtained from EDX performed on the cross-section of the membrane (labelled according to the definition of FIG. 1) are shown in FIG. 17.

Following incorporation into the membrane, chlorambucil was extracted and subjected to HPLC analysis. A known amount of the incorporated Chlorambucil/porous silicon (typically 10-15 mg, dependent on the level of incorporation) was placed into a volumetric flask and made up to a volume with 100 ml of ethanol, shaken and sonicated for 30 minutes at 30° C. From this stock solution 25 ml were transferred by pipette to a 100 ml volumetric flask to give the sample solution. Prior to analysis by HPLC the sample was filter through a 0.45 micron filter.

The chromatographic conditions used for this analysis were:—

| Parameter | Condition |
|---|---|
| Mobile Phase | Methanol:Water:Acetonitrile:Glacial Acetic Acid 58:39:2.5:0.5 |
| Column | Waters Xterra RP18 3.5 μm 4.6 × 100 mm |
| Column Temperature | 35° C. |
| Sample chamber temperature | 15° C. |
| Injection Volume | 20 μl |
| UV absorbance | 257 nm |
| Needle Wash | Methanol:Water 50:50 |
| Run Time | 10 minutes |
| Retention time Chlorambucil | Approximately 5.0 minutes |
| Calibration Type | Using external Chlorambucil standards to create linearity curve |

Figure 5:
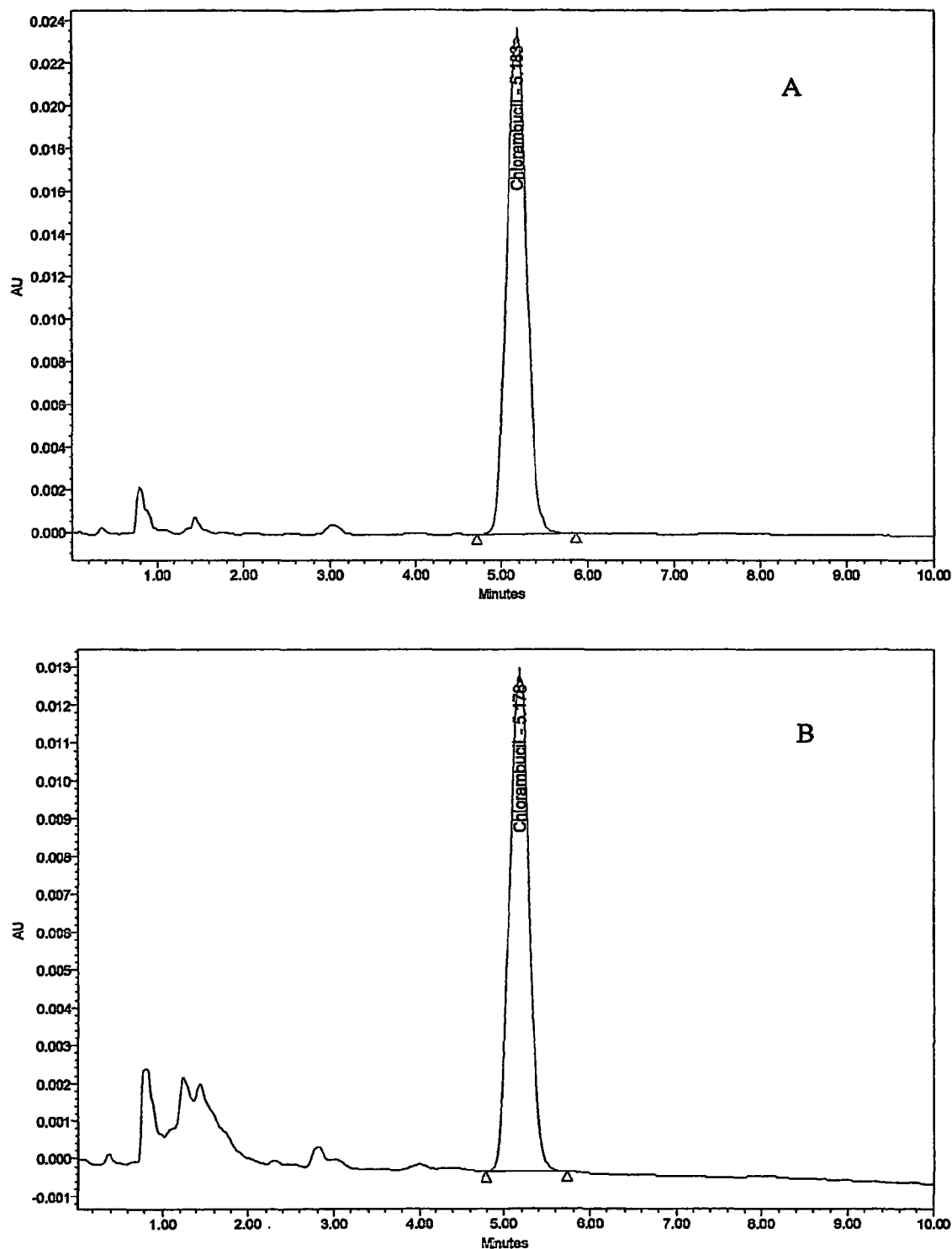
FIG. 5 shows an HPLC analysis of chloambucil, standard in ethanol(A) and after incorporation and extraction from porous silicon(B)

The results (FIG. 5) demonstrated that the compound could be incorporated and released from the semiconductor material without significant degradation. An unchanged position of the single dominant peak labelled chlorambucil is the main indicator that insignificant degradation has occurred as a result of loading into and subsequent release from porous silicon. Appreciable degradation would have resulted in additional intense peaks around the parent peak at 5.2 minutes "retention time" in the spectrum. The large number of small peaks between 0 and 3.2 minutes retention time are unrelated to chlorambucil.

2. Amitriptyline HCl (Melting Point 198-200° C.)

Loading was performed by placing the pre-dissolved amitriptyline solution (in ethanol) on the porous silicon membrane, heated gently at 90° C. for 10 minutes. After drug loading and washing, its weight increased to 38.78 mg (from 25.18 mg) which is equivalent to 35.07% w/w. Thus the drug occupied (74.07/drug density) % of the pore volume available.

Weight of unloaded flake = 25.18 mg

Density = $d_{AMT}$ g cm$^{-3}$

Void volume = {25.18/479.60 mg} × 814.75 mg/{density of silicon}
= 0.01836 cm$^3$ Maximum loading capacity = 0.01836 cm$^3$ × $d_{AMT}$ g cm$^{-3}$
= 18.36 $d_{AMT}$ mg Loading & washing $w_1$ = 38.35 mg $w_2$ = 38.77 mg $w_3$ = 38.78 mg equivalent to 35.07% w/w % loading capacity (w/v) = {38.78 − 25.18}/{18.36 $d_{AMT}$} × 100
= 74.07/$d_{AMT}$ %

Figure 6:
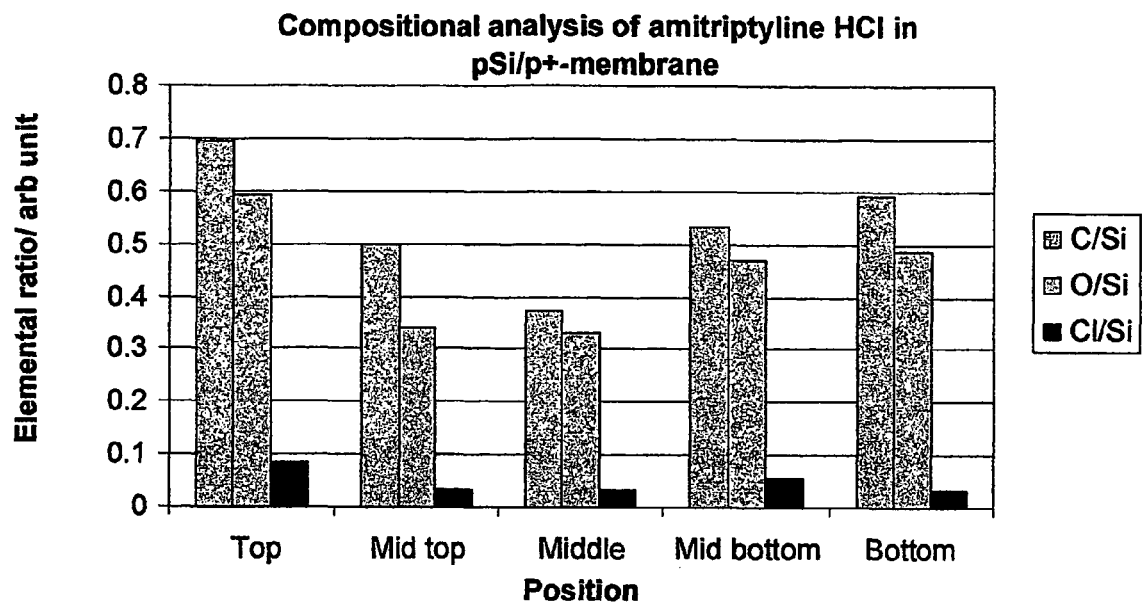
FIGS. 6 to 14 show the compositional analysis of a porous silicon p+ membrane impregnated with the following beneficial organic substances, as determined by SEM-EDX:—

Compositional analysis of the impregnated membrane, using the SEM-EDX method (FIG. 6) shows a high loading for amitriptyline, based on the elemental ratios of C/Si. Chlorine is observed through EXD along the cross-section of the membrane, suggesting that the drug is still a produg as it is still well complexed with HCl. However, this complexation induces the adsorption of water from the atmospheric moisture, which subsequently brings high O/Si content in the structure.

3. S-(+)-Ibuprofen(Melting Point 75-78° C.)

Impregnation was performed by placing the pre-dissolved ibuprofen solution (in ethanol) on membrane under the applied gentle heat at 90° C. for 20 minutes. The resulting weight of loading gave 19.50 mg (from 11.57 mg) equivalent to 40.67% w/w. This occupied nearly (89.54/drug density) % of the pore volume available.

Weight of unloaded flake = 11.57 g mg

Density = $d_{Ibu}$ cm$^{-3}$

Void volume = {11.57/460.06 mg} × 820.57 mg/{density of silicon}
= 0.0088568 cm$^3$ Maximum loading capacity = 0.0088568 cm$^3$ × $d_{dox}$ g cm$^{-3}$
= 8.8568 $d_{Ibu}$ mg Loading & washing $w_1$ = 19.50 mg equivalent to 40.67% w/w % loading capacity (w/v) = {19.50 − 11.57}/{8.8568 $d_{Ibu}$} × 100
= 89.54/$d_{Ibu}$ %

Figure 7:
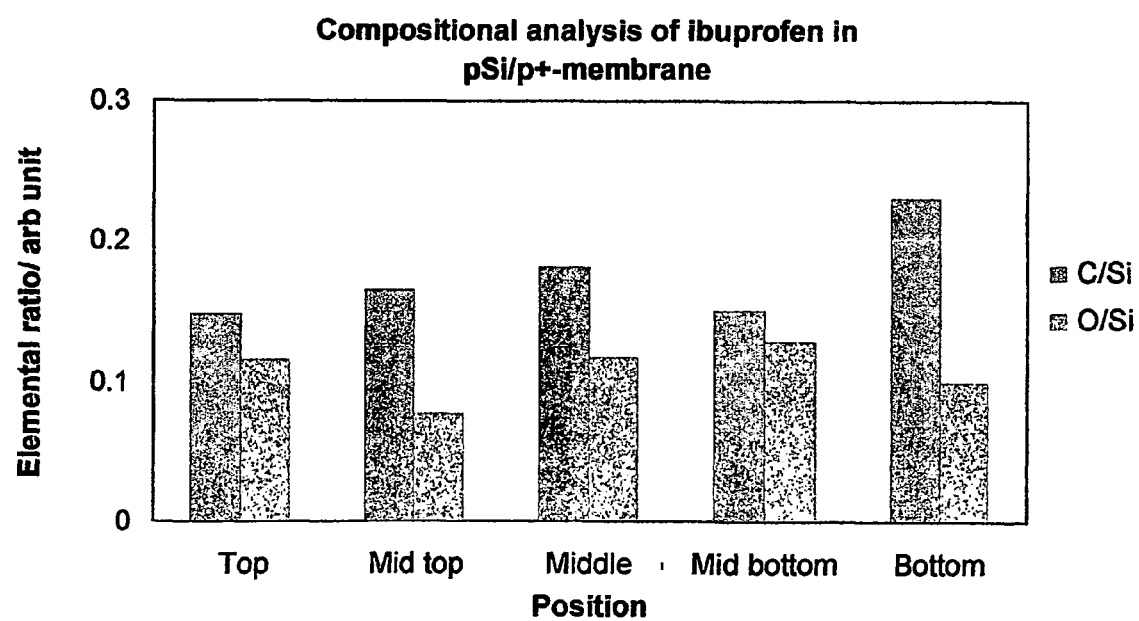

Compositional analysis of the impregnated membrane, using the SEM-EDX method (FIG. 7) shows a homogenous loading for ibuprofen with the clear evidence of observed carbon throughout the membrane.

4. Procaine (Melting Point 153-156° C.)

Impregnation was conducted by placing the dissolved procaine (in EtOH:dH$_2$O 1:1) on the porous silicon/p+ membrane, heated gently at 110° C. (above boiling point of dH$_2$O) until the solution becomes dried for 25 minutes. The resultant weight of loading was equivalent to 35.33% w/w or 71.38% w/v Weight of unloaded flake = 9.70 mg Density = $d_{Pro}$ g cm$^{-3}$ Void volume = {9.70/460.06 mg} × 820.57 mg/{density of silicon}
= 0.0074253 cm$^3$ Maximum loading capacity = 0.0074253 cm$^3$ × $d_{Pro}$ g cm$^{-3}$
= 7.4253 $d_{Pro}$ mg Loading & washing $w_1$ = 16.01 mg $w_2$ = 15.00 mg equivalent to 35.33% w/w % loading capacity (w/v) = {15.00 − 9.70}/{7.4253 $d_{Pro}$} × 100
= 71.38/$d_{Pro}$ %

Figure 8:
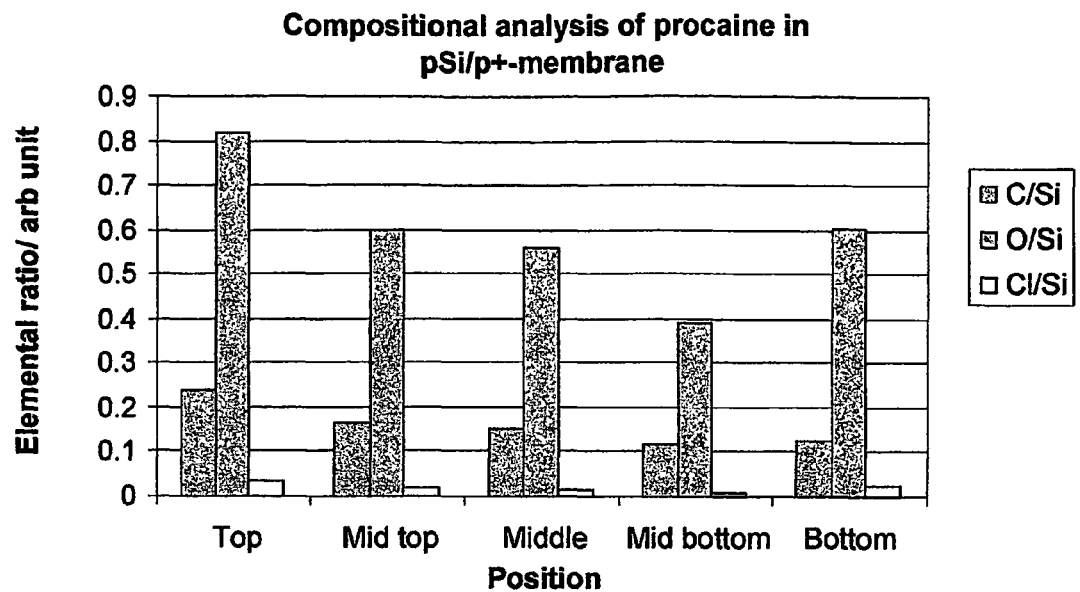

Similarly to amitriptyline HCl, the procaine loaded in the pSi pores tends to adsorb the moisture from the air, and a very high content of oxygen was shown to be present through the cross-section (FIG. 8).

5. Levamisole HCl (Melting Point 230-233° C.)

Impregnation was performed by placing the dissolved levamisole (in EtOH:dH$_2$O 1:1) on the porous silicon p+ membrane and heating gently at 110° C. (above boiling point of dH$_2$O) until the solution becomes dried for 25 minutes. The weight gain after the loading accounts for 32.93% w/w, which is equivalent to the drug occupying the pore volume at (64/drug density) %.

Weight of unloaded flake = 9.35 mg

Density = $d_{Lev}$ g cm$^{-3}$

Void volume = {9.35/460.06 mg} × 820.57 mg/{density of silicon}
= 0.0071574 cm$^3$ Maximum loading capacity = 0.0071574 cm$^3$ × $d_{Lev}$ g cm$^{-3}$
= 7.1574 $d_{Lev}$ mg Loading & washing $w_1$ = 12.87 mg $w_2$ = 13.94 mg equivalent to 32.93% w/w % loading capacity (w/v) = {13.94 − 9.35}/{7.1574 $d_{Lev}$} × 100
= 64.13/$d_{Lev}$ %

Figure 9:
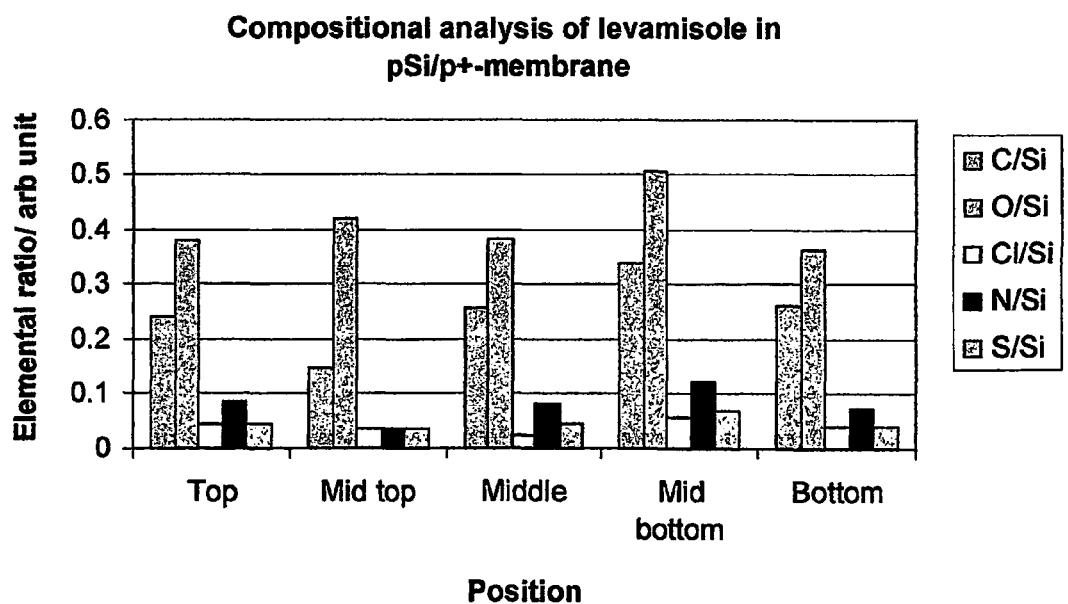

As can be seen from the compositional analysis using SEM-EDX (FIG. 9), the Cl signal was detected throughout the cross-section suggesting that following impregnation, the compound still existed as a prodrug 6. Plumbagin (Melting Point 78-79° C.)

Plumbagin is a natural yellow pigment found in plants of Plumbagineae and Droseracea families Impregnation was performed by placing plumbagin, dissolved in ethanol, on the porous silicon membrane, and the heat was applied gently at 90° C. for 20 minutes. The weight gain accounts for 34.68% w/w, equivalent to an occupied pore volume of (98.50/drug density) %

Weight of unloaded flake = 13.28 mg

Density = $d_{Plum}$ g cm$^{-3}$

Void volume = {13.28/460.06 mg} × 820.57 mg/{density of silicon}
= 0.0101658 cm$^3$ Maximum loading capacity = 0.0101658 cm$^3$ × $d_{Plum}$ g cm$^{-3}$
= 10.1658 $d_{Plum}$ mg Loading & washing $w_1$ = 17.33 mg $w_2$ = 20.33 mg equivalent to 35.68% w/w % loading capacity (w/v) = {20.33 − 13.28}/{7.1574 $d_{Plum}$} × 100
= 98.50/$d_{Plum}$ %

Figure 10:
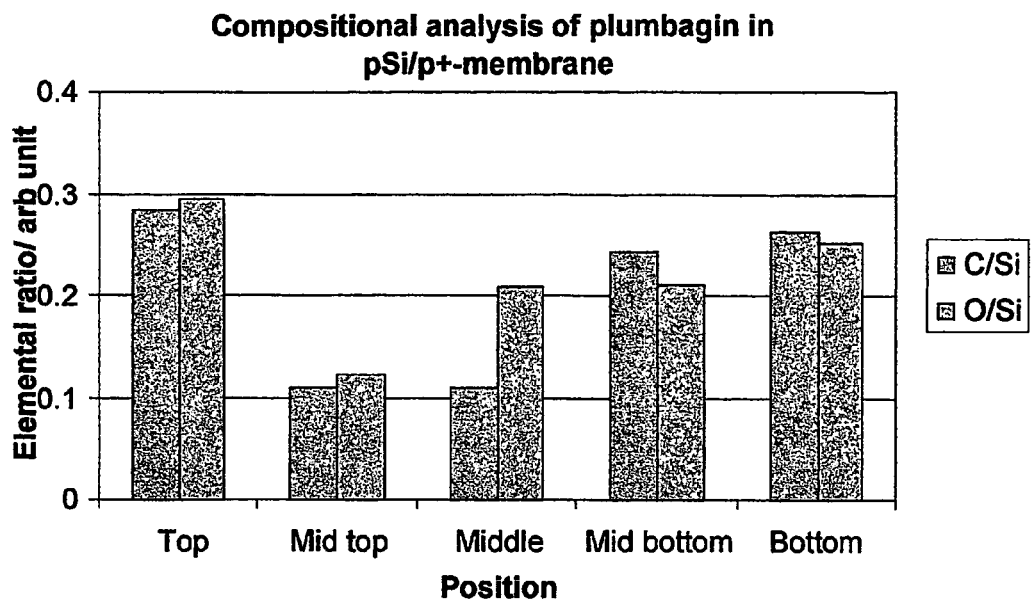

FIG. 10 shows the compositional analysis, as determined by SEM-EDX, of plumbagin impregnated membrane. From this it can be seen that fairly high loading is obtained for the plumbagin, with reference to the C/Si content.

7. Cyclophosohamide (Melting Point 41-45° C.)

Impregnation was performed by a direct loading-melting method with heating melting around 60° C. for 20 minutes. After the loading and washing, the weight obtained increasing from 9.68 mg to 17.41 mg, equivalent to w/w of 44.4%. Thus, the drug occupied the pore volume at (104/drug density) %.

Weight of unloaded flake = 9.68 mg

Density = $d_{Cyc}$ g cm$^{-3}$

Void volume = {9.68/460.06 mg} × 820.57 mg/{density of silicon}
= 0.00741 cm$^3$ Maximum loading capacity = 0.00741 cm$^3$ × $d_{Cyc}$ g cm$^{-3}$
= 7.41 $d_{Cyc}$ mg Loading & washing $w_1$ = 17.41 mg equivalent to 44.40% w/w % loading capacity (w/v) = {17.41 − 9.68}/{7.41 $d_{Pro}$} × 100
= 104.32/$d_{Pro}$ %

Figure 11:
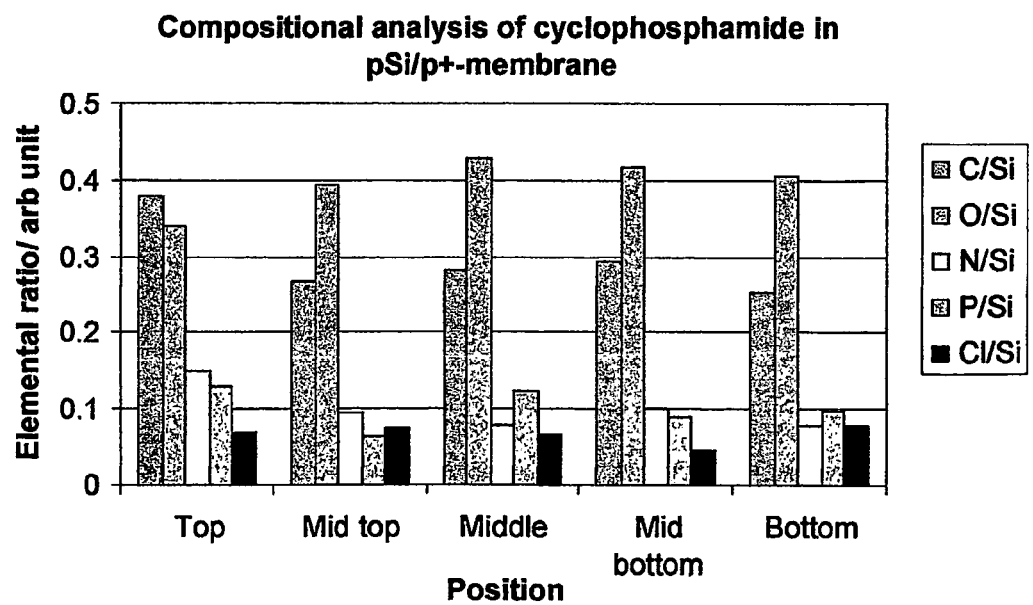

From the SEM-EDX compositional analysis (FIG. 11) it can be seen that all elements in the cyclophosphamide were observed clearly (especially for elements P and N), implying that the drug is loaded in the pores throughout the thickness of the membrane 8. Busulfan (Melting Point 114° C.)

Busulfan was pre-dissolved in a solution of ethanol and water (1:1), placed on the porous silicon membrane and heated at 120° C. for 30 minutes. Following washing, the weight gain was determined to be 37.54% w/w, equivalent to 78.53/drug density % w/v Weight of unloaded flake = 8.80 mg Density = $d_{bus}$ g cm$^{-3}$ Void volume = {8.80/460.06 mg} × 820.57 mg/{density of silicon}
= 0.0067364 cm$^3$ Maximum loading capacity = 0.0067364 cm$^3$ × $d_{Bus}$ g cm$^{-3}$
= 6.7364 $d_{Bus}$ mg Loading & washing $w_1$ = 10.67 mg $w_2$ = 14.09 mg equivalent to 37.54% w/w % loading capacity (w/v) = {14.09 − 8.80}/{6.7364 $d_{Bus}$} × 100
= 78.53/$d_{Bus}$ %

Figure 12:
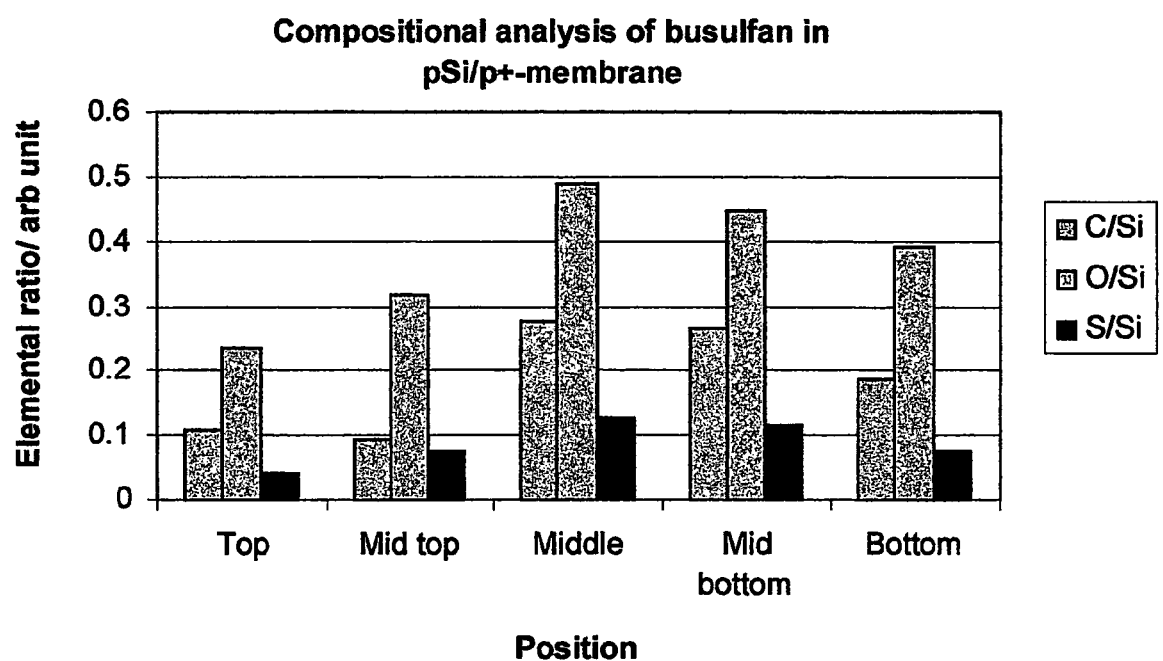

SEM-EDX compositional analysis of the pure drug gave elemental C:O:S in the expected ratios of 3:3:1. C, O and S signals were found clearly throughout the EDX investigation (FIG. 12).

9. Dexamethasone (Melting Point 255° C.)

Dexamethasone was pre-dissolved in a solution of ethanol and dH2O (1:1), placed on the porous silicon membrane and heated at 130° C. for 30 minutes. Following washing, the weight gain was determined to be 31.52% w/w or 60.14/drug density % w/v Weight of unloaded flake = 6.43 mg Density = $d_{Dex}$ g cm$^{-3}$ Void volume = {6.43/460.06 mg} × 820.57 mg/{density of silicon}
= 0.0049222 cm$^3$ Maximum loading capacity = 0.0049222 cm$^3$ × $d_{Dex}$ g cm$^{-3}$
= 4.9222 $d_{Dex}$ mg Loading & washing $w_1$ = 9.65 mg $w_2$ = 9.39 mg equivalent to 31.52% w/w % loading capacity (w/v) = {9.39 − 6.43}/{4.9222 $d_{Dex}$} × 100
= 60.14/$d_{Dex}$ %

Figure 13:
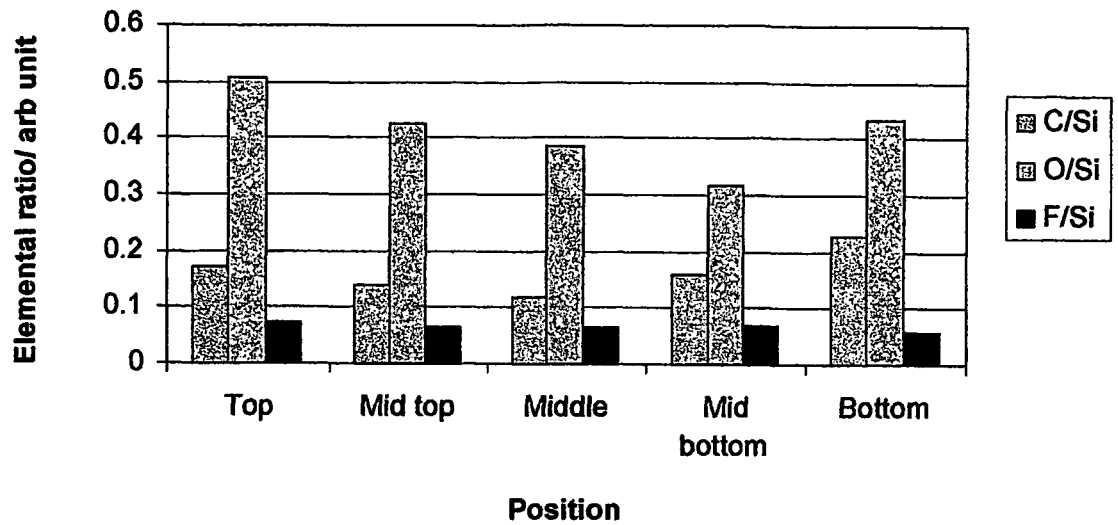

The compositional analysis of dexamethasone in the porous silicon membrane (FIG. 13) demonstrates that loading was fairly homogenous throughout the membrane. The F/Si ratio is particularly used to identify the loading of dexamethasone in the membrane, in conjunction with the C/Si ratio.

10. Lauric Acid (Melting Point 44° C.)

Impregnation was performed by the direct loading-melting method, with the applied heat at temperature 60° C. on the hot plate for 20 minutes. Following washing, the weight gain was determined to be 42.57% w/w or 55.62/drug density % w/v Weight of unloaded flake = 12.59 mg Density = $d_{Lau}$ g cm$^{-3}$ Void volume = {12.59/460.06 mg} × 820.57 mg/{density of silicon}
= 0.0096376 cm$^3$ Maximum loading capacity = 0.0096376 cm$^3$ × $d_{Lau}$ g cm$^{-3}$
= 9.6376 $d_{Lau}$ mg -continued Loading & washing $w_1 = 17.95$ mg equivalent to 42.57% w/w % loading capacity $(w/v) = \{17.95 - 12.59\}/\{9.6376 \, d_{Lau}\} \times 100$
$= 55.62/d_{Lau}$ %

Figure 14:
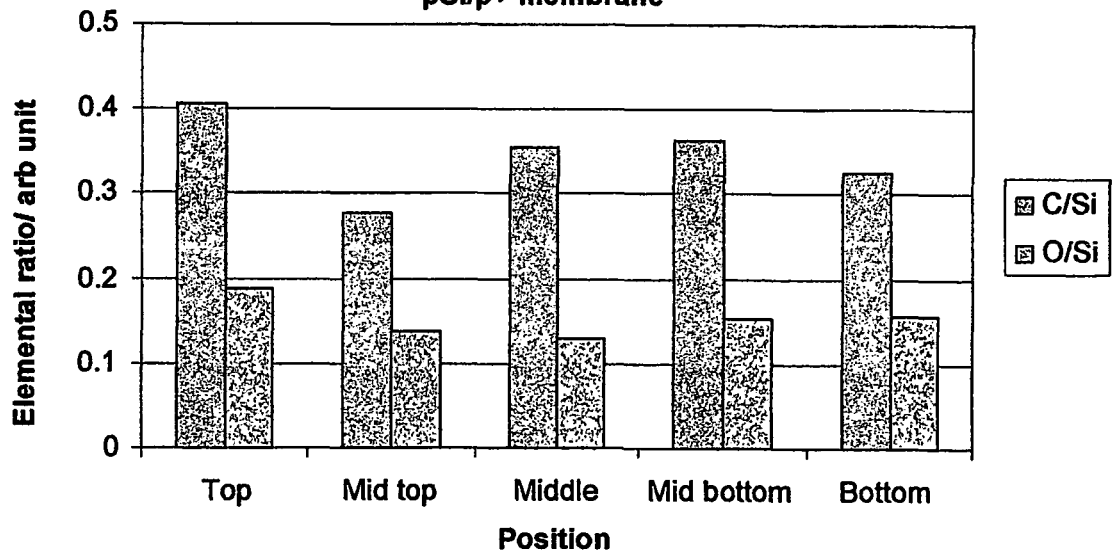

SEM-EDX compositional analysis of the impregnated membrane (FIG. 14) demonstrated that C was found throughout the cross section of the membrane with a C/Si ratio of approximately 0.35, suggesting high loading of lauric acid.

11. α-tocopherol (Vitamin E, Boiling Point 200° C.)

Vitamin E has a density of 0.95 g cm$^{-3}$ so for a 63% porosity silicon matrix the maximum w/w loading capacity is 41%. The loading was performed by applying directly the liquid form of vitamin E on to the pSi/p+ membrane with gentle heating at 70° C. for 20 minutes. The weight of the unloaded flake was 58.83 mg. After the drug loading and washing its weight increased to 93.67 mg equivalent to a w/w loading of 37%. Thus the drug occupied 88% of the pore volume available, Weight of unloaded flake = 58.83 mg Purity of vitamin E (Sigma) = 97%

Density = 0.95 g cm$^{-3}$

Figure 15:
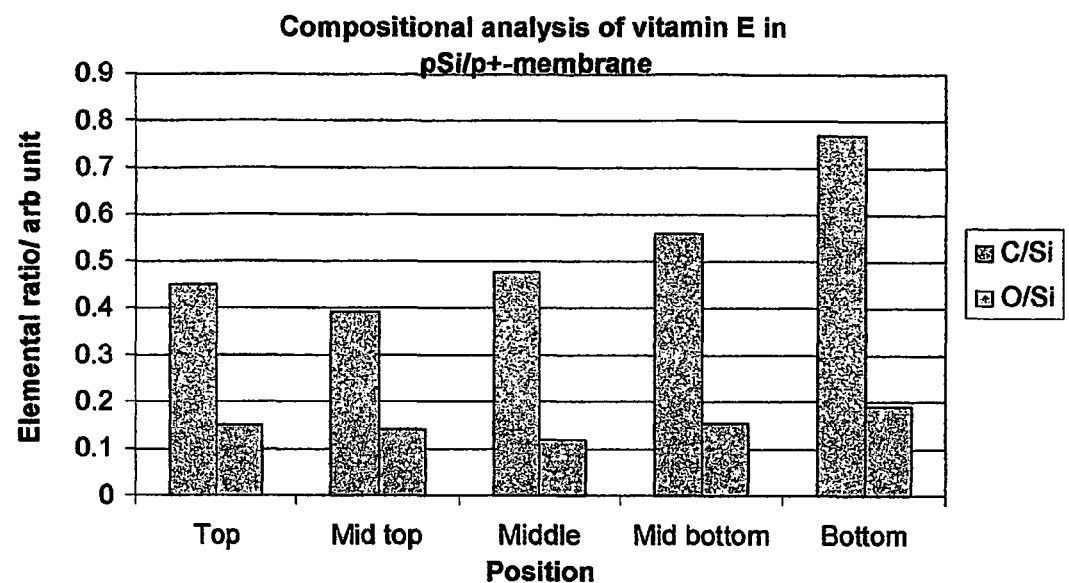

Void volume = {58.83 mg/479.60 mg} × 814.75 mg/{density of silicon}
$= 0.04289$ cm$^3$ Maximum loading capacity = 0.04289 cm$^3$ × 0.97 × 0.95 g cm$^{-3}$
$= 39.5259$ mg Loading & washing $w_1 = 103.96$ mg $w_2 = 94.99$ mg $w_3 = 92.31$ mg $w_4 = 93.67$ mg equivalent to 37.19% w/w % loading capacity $(w/v) = \{93.67 - 58.83\}/39.5259 \times 100$
$= 88.14\%$ From the high elemental ratios of C/Si (~0.53) and O/Si (~0.15) in the compositional analysis (FIG. 15) it can be seen that Vitamin E is found throughout the membrane.

12. Vitamin K

Vitamin K used has a density of 0.984 g cm$^{-3}$ so for a 63% porosity silicon matrix the maximum w/w loading capacity is 42%. The loading was performed by applying directly the liquid form of vitamin K on membrane with gentle heating at 70° C. for 20 minutes. The weight of the unloaded flake was 31.90 mg. After the drug loading and washing its weight increased to 49.92 mg equivalent to a w/w loading of 36%. Thus the drug occupied 80% of the pore volume available.

Weight of unloaded flake = 31.90 mg

Purity of vitamin K (Sigma) = 98%

Density = 0.984 g cm$^{-3}$

-continued

Figure 16:
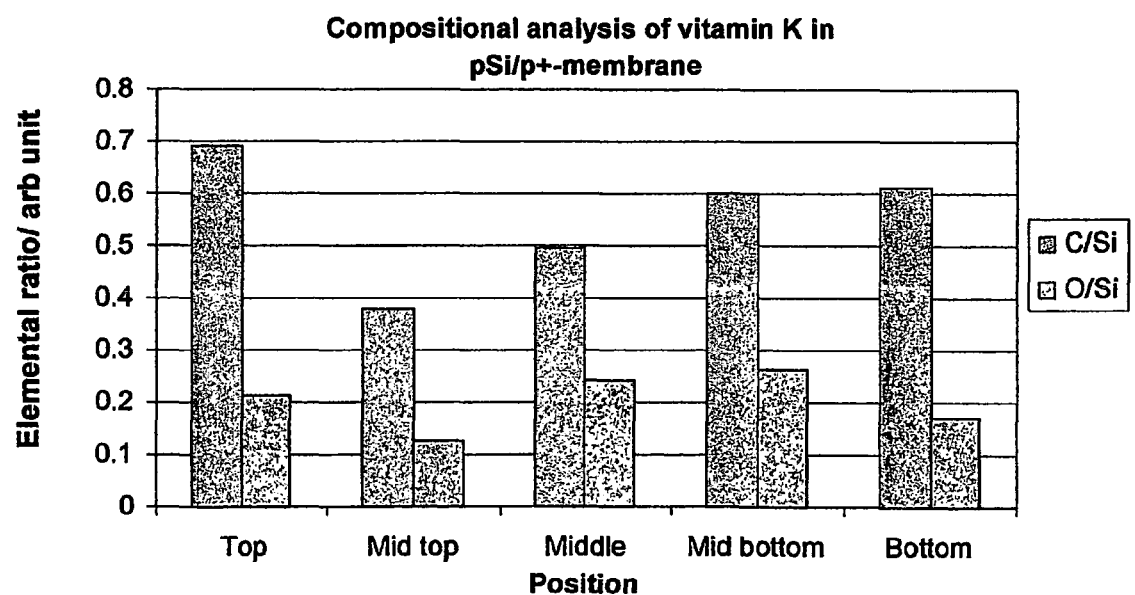

Void volume = {31.90 mg/479.60 mg} × 814.75 mg/{density of silicon}
$= 0.02326$ cm$^3$ Maximum loading capacity = 0.02326 cm$^3$ × 0.98 × 0.984 g cm$^{-3}$
$= 22.43$ mg Loading & washing $w_1 = 49.50$ mg $w_2 = 49.92$ mg equivalent to 36.10% w/w % loading capacity $(w/v) = \{49.92 - 31.90\}/22.43 \times 100$
$= 80.34\%$ Vitamin K was shown to be loaded Well in the pSi/p+ membrane, based on the high elemental ratios of C/Si~0.56 and O/Si~0.20 (FIG. 16)

13. Medroxyprogesteron Acetate (Melting Point 207° C.)

Following the method of Example 2, impregnation of a porous silicon membrane by a solution of the drug in acetone gave a drug loading equivalent to 19.81% w/w.

14. Rifamnicin (Melting Point 183-188° C.)

Loading was performed by placing a solution of the drug in ethanol on the porous silicon membrane and removing the solvent by rotary evaporation. A drug loading equivalent to 19% w/w was obtained.

15. Paclitaxel (Melting Point 216-217° C.)

Impregnation of the porous silicon membrane by a solution of the drug in ethanol on the using the rotary evaporation method gave a drug loading equivalent to 16.71% w/w.

SEM-EDX analysis of the paclitaxel impregnated porous silicon/p+ membrane (166 μm thick) confirms that the paclitaxel is substantially uniformly distributed throughout the membrane, as can be seen from the EDX spectra performed on the cross-section of the membrane at a depth of (A) 80 μm and (B) 145 μm from the surface of the material presented in FIG. 18.

HPLC analysis confirms that the compound is incorporated into and release from the porous silicon material without significant degradation.

The dissolution of the paclitaxel impregnated porous silicon membrane (weight of sample equivalent to 2 mg porous silicon) was studied in a total media replacement dissolution apparatus with PBS (phosphate buffer solution, pH 7.4) as dissolution medium at ambient temperature using UV spectroscopy (230 nm). At each time point (each day) the impregnated membrane was transferred from one 4 ml PBS containing bijou into a fresh 4 ml PBS containing bijou.

FIG. 19 shows the UV profiles obtained from eluted samples on days 2, 13 and 20 (A-C respectively). From these results it can be seen that the absorption profile of the eluted drug does not alter over the period of 20 days, suggesting that the drug eluted from the loaded sample is not substantially degraded over this time.

FIG. 20 shows the graph obtained for the cumulative release of paclitaxel from the impregnated membrane measured over a period of 30 days. From this it can clearly be seen that sustained, controlled release of paclitaxel is achieved, the release rate being approximately constant for the first 7 days and slowing thereafter until after 30 days, 95% of the drug has been recovered. Particularly notably, no initial 'burst' in the rate of release is seen; this represents a significant advantage over other controlled release formulations.

(b) In Vivo Studies

The effects of intra-tumoural administered chlorambucil loaded porous silicon and paclitaxel loaded porous silicon formulations, prepared as described in Examples 1 and 15 above, on tumour growth in mice were studied. In both cases, effective tumour regression was observed without significant mortality, even when the drug is administered at a dosage level greater than the LD50 of the corresponding free drug.

Chlorambucil

Studies on animal models were carried out in the animal laboratory of the Dept of Experimental Surgery of the Singapore General Hospital with the approval by the Ethical Committee of the Singapore General Hospital.

The following protocol was adopted:—
1. Culture of human cells and implantation of the tumour cells as solid tumours in nude mice: The carcinoma cell-line was cultured in RPMI and Ham's F-12 media respectively with 10% fetal calf serum in a $CO_2$ incubator and subcultured every two to three days until growing to a number enough for implantation in animals. The cells were then implanted as solid tumors in nude mice]. The cells were collected in HBSS (balanced salt solution). One hundred microliters of cell suspension in HBSS ($5 \times 10^6$ cells) was injected subcutaneously into right gluteal region of nude mice (female, 6 to 9 week old nude mice with average body weight of 25 g, housed in pathogen-free conditions) using a 25-gauge needle.
2. Animals groups: Animals were randomly grouped into control 1 (injected with peanut oil), control 2 (injected with porous silicon without drug), free chlorambucil (drug injected without porous silicon directly into tumour or injected via intraperitoneal route) and chlorambucil impregnated porous silicon groups. Each group included 16 to 20 animals.
3. Injection of chlorambucil impregnated porous silicon in transplanted tumours: On day 14 after implantation of tumours (diameter of the tumour about 1 cm), the chlorambucil impregnated formulation was applied to the centre of the tumours.
4. Tumour volumetrics: The sizes of implanted tumours in nude mice was estimated every 3 days. The largest and smallest diameters were measured by a vernier caliper and tumour volumes estimated according the formula: $V = 1/2\, ab^2$, where a and b are largest and smallest tumour diameters respectively, and V is the tumour volume in $cm^3$.

The effects of intra-tumoural administered chlorambucil loaded porous silicon on the growth of the tumour was studied and compared with control and systemic therapy groups. The body weight of the animals was estimated by subtracting the tumour volume (cm3) from the total body weight (g) every 3 days. The survival time of each experimental animal was recorded.

The results of the relative tumour volumes over time presented graphically in FIG. 21 show that chlorambucil loaded into porous silicon (CBS) was very effective in causing tumour regression depending on the dosage used. These results are from anodisation derived porous silicon flake loaded with chlorambucil (360 ug or 720 ug) by the melting solvent method and subsequently subjected to particle size reduction to about 20 microns by grinding in a pestle and mortar for 1 hour In another series of experiments using the same tumour model, higher dosage of chlorambucil (1500 ug), delivered by porous silicon and injected directly into the tumour, significantly decreased the size of the tumour when compared with the animals that had received no treatment (control group). Flank tumour growth was delayed by 12 weeks when compared with the animals that had received no treatment (FIG. 22). In contrast, intratumour delivery of chlorambucil using the same dosage ($2 \times LD_{50}$) resulted in a 90% animal mortality rate. An increase of the drug dosage from 720 ug (LD50) to 1.5 mg (2×LD50) led to 20% mortality in the CBS groups suggesting the possibility of prolonged tumour exposure to the drug while minimizing the drug's dose-limiting, systemic side effects. In contrast, the administration of similar amounts of Chlorambucil without porous silicon resulted in a mortality rate of 50% (720 ug) to 90% (1500 ug). The results of these studies showed a significantly prolonged survival rate for the group treated according to the method of the invention. Moreover, treatment by locally administered chlorambucil loaded porous silicon produced long-term survivors Paclitaxel The effect of paclitaxel loaded porous silicon on the subcutaneous growth of the human breast carcinoma MCF7 in nude mice was investigated and compared to a control group of mice injected with peanut oil excipient only. Studies were performed at the University of Nottingham. The following protocol was adopted:—

Implantation method: The tumour line was maintained in serial passage in nude mice. For the therapy study, donor mice were sacrificed and the tumours excised. The tumour was finely minced, and 3 $mm^3$ sections implanted subcutaneously into the flank of MF1 nude mice under suitable anaesthesia. Animals were examined regularly for the appearance of tumours. When measurable tumours had established, the mice were assigned to the treatment groups by size to give a representative distribution of sizes within each group. Tumour size was evaluated three times weekly.

The treatment group received 100 ul of formulated compound (paclitaxel loaded into porous silicon) injected directly to tumour. The control group received 100 ul of peanut oil only.

From the results of the determination of tumour cross-sectional area over time presented graphically in FIG. 23, it can be seen that retardation of tumour growth is observed in mice treated with paclitaxel loaded porous silicon (B) when compared with the control group (A).

The invention claimed is:

1. A composite material comprising a porous semiconductor impregnated with at least one beneficial organic substance to a pore depth from the surface of the semiconductor of at least 5 microns, wherein the beneficial organic substance is present in an amount of at least 15% by weight, based on the weight of the material.

2. A material according to claim 1 wherein the porous semiconductor is impregnated with at least one beneficial organic substance to a pore depth from the surface of at least 50 microns.

3. A material according to claim 1 wherein the porous semiconductor is doped or undoped silicon, germanium, silicon carbide or silicon nitride.

4. A material according to claim 3 wherein the porous semiconductor is silicon.

5. A material according to claim 4 wherein the silicon is resorbable.

6. A material according to claim 5 where the silicon is mesoporous.

7. A material according to claim 4 wherein the porous silicon has a porosity of from 40% to 90%.

8. A material according to claim 1 wherein the beneficial organic substance has a solubility in aqueous media of no more than 10 mg/mL at a pH range 1-7.

9. A material according to claim 1 wherein the beneficial organic substance has a melting point of below 300° C.

10. A material according to claim 9 wherein the beneficial organic substance has a melting point of below 100° C.

11. A material according to claim 1 wherein the beneficial organic substance is selected from chlorambucil, amitriptyline, ibuprofen, procaine, levamisole, plumbagin, cyclophosphamide, busulfan, dexamethasone, lauric acid, medroxy progesterone acetate, vitamin K, vitamin E, paclitaxel and rifampicin or a mixture thereof.

12. A material according to claim 1 wherein the beneficial organic substance is present in an amount of from 15% to 85% by weight, based on the weight of the material.

13. A material according to claim 1 wherein the beneficial organic substance is distributed substantially uniformly through the pores of the semiconductor.

14. A material according to claim 1 wherein the beneficial organic substance is selected from antibodies, peptides and genetic constructs.

* * * * *